(12) United States Patent
Bay et al.

(10) Patent No.: US 9,657,074 B2
(45) Date of Patent: May 23, 2017

(54) ENZYMATIC LARGE-SCALE SYNTHESIS OF MUCIN GLYCONJUGATES, AND IMMUNOGENIC APPLICATIONS THEREOF

(75) Inventors: Sylvie Bay, Paris (FR); Teresa Freire, Montevideo (UY); Claude Leclerc, Paris (FR); Richard Lo-Man, Paris (FR)

(73) Assignees: Institut Pasteur, Paris (FR); Institut National de la Santé et de la Recherche Médicale (INSERM), Paris (FR); Centre National de la Recherche Scientifique, Paris (FR)

( * ) Notice: Subject to any disclaimer, the term of this patent is extended or adjusted under 35 U.S.C. 154(b) by 1622 days.

(21) Appl. No.: 12/160,605

(22) PCT Filed: Feb. 23, 2006

(86) PCT No.: PCT/EP2006/002577
§ 371 (c)(1),
(2), (4) Date: Nov. 10, 2009

(87) PCT Pub. No.: WO2007/079783
PCT Pub. Date: Jul. 19, 2007

(65) Prior Publication Data
US 2010/0272707 A1 Oct. 28, 2010

(30) Foreign Application Priority Data
Jan. 13, 2006 (EP) .................................... 06290091

(51) Int. Cl.
A61K 38/00 (2006.01)
C07K 14/47 (2006.01)
A61K 39/00 (2006.01)

(52) U.S. Cl.
CPC .......... *C07K 14/4727* (2013.01); *A61K 39/00* (2013.01); *A61K 39/0011* (2013.01)

(58) Field of Classification Search
CPC ................................................ A61K 39/0011
USPC .................... 530/300, 350; 424/185.1, 277.1
See application file for complete search history.

(56) References Cited

U.S. PATENT DOCUMENTS

2003/0138859 A1* 7/2003 Barbera-Guillem et al. ............................ 435/7.21
2008/0064059 A1* 3/2008 Schultz .................... C12N 9/93 435/68.1

FOREIGN PATENT DOCUMENTS

WO   WO2004069136 A2 *  8/2004

OTHER PUBLICATIONS

Skolnick and Fetrow. From genes to protein structure and function: novel applications of computational approaches in the genomic era. Trends in Biotechnology, 2000. vol. 18, pp. 34-39.*
Burgess, Shaheen, Ravera, Jaye, Donohue, and Winkles. Possible dissociation of the heparin binding and mitogenic activities of heparin binding (acidic fibroblast) growth factor-1 from its receptor binding activities by site directed mutagenesis of a single lysine residue. Journal of Cell Biology, 1990. vol. 111, pp. 2129-2138.*
Lazar, Watanabe, Dalton, and Sporn. Transforming growth factor alpha: mutation of aspartic acid 47 and leucine 48 results in different biological activities. Molecular and Cellular Biology, 1988. vol. 8, pp. 1247-1252.*
De Bolòs et al. (Int. J. Cancer. Jul. 17, 1998; 77 (2): 193-9).*
Brockhausen et al. (Biol. Chem. Feb. 2001; 382 (2): 219-32).*
Van Klinken et al. (Am. J. Physiol. Aug. 1997; 273 (2 Pt 1): G296-302).*
Grogan et al. (Annu. Rev. Biochem. 2002; 71: 593-634).*
Pratt et al. (Chem. Soc. Rev. Jan. 2005; 34 (1): 58-68).*
Freire et al. (Cancer Res. Sep. 1, 2005; 65 (17): 7880-7).*
Hojo et al. (Curr. Protein Pept. Sci. Jul. 2000; 1 (1): 23-48).*
Sames et al. (Nature. Oct. 9, 1997; 389 (6651): 587-910).*
Freire et al. (J. Biol. Chem. Mar. 11, 2011; 286 (10): 7797-811).*
Freire et al. (Glycobiology. May 2006; 16 (5): 390-401).*
Reis et al. (J. Histochem. Cytochem. Mar. 2000; 48 (3): 377-88).*
Stadie et al. (Eur. J. Biochem. 1995; 229: 140-7).*
Nishimori et al. (Cancer Res. 1994; 54: 3738-44).*
Sorensen et al. (Glycobiology. 2006; 16 (2): 96-107).*
Hanisch et al. (J. Biol. Chem. 1999; 274 (15): 9946-54).*
Freire et al. (Cancer Res. 2005; 65 (17): 7880-7).*
Freire, Teresa et al., "Molecular Basis Of Incomplete O-Glycan Synthesis In MCF-7 Breast Cancer Cells: Putative Role Of MUC6 In Tn Antigen Expression", Cancer Research, vol. 65, No. 17, pp. 7880-7887 (2005).
Ten Hagen, Kelly G. et al., "All In The Family: The UDP-GalNac: Polypeptide N-Acetylgalactosaminyltransferases", Glycobiology, vol. 13, No. 1, pp. 1R-16R (2003).
Bartman, Allen et al., "Aberrant Expression Of MUC5AC And MUC6 Gastric Mucin Genes In Colorectal Polyps", Int. J. Cancer, vol. 80, pp. 210-218 (1999).
De Bolos, Carme et al., "MUC6 Apomucin Shows A Distinct Normal Tissue Distribution That Correlates With Lewis Antigen Expression In The Human Stomach", Gastroenterology, vol. 109, No. 3, pp. 723-734 (1995).
Guillem, Philippe et al., "Mucin Gene Expression And Cell Differentiation In Human Normal, Premalignant and Malignant Esophagus", Int. J. Cancer, vol. 88, pp. 856-861 (2000).
Hamamoto, Atsushi et al., "Aberrant Expression Of The Gastric Mucin MUC6 In Human Pulmonary Adenocarcinoma Xenografts", International Journal of Oncology, vol. 26, pp. 891-896 (2005).
Nishiumi, Noboru et al., "Use of 11p15 Mucins as Prognostic Factors In Small Adenocarcinoma Of The Lung", Clinical Cancer Research, vol. 9, pp. 5616-5619 (2003).
Pereira, M. B. et al., "Immunohistochemical Study Of The Expression Of MUC5AC and MUC6 In Breast Carcinomas And Adjacent Breast Tissues", J Clin. Pathol., vol. 54, pp. 210-213 (2001).

* cited by examiner

*Primary Examiner* — Stephen Rawlings
(74) *Attorney, Agent, or Firm* — Arrigo, Lee & Guttman LLP

(57) ABSTRACT

The present invention relates to mucin glycoconjugates, and to a process of producing mucin glycoconjugates. It relates to the biological, pharmaceutical and medical applications thereof. The invention notably provides mucin glycoconjugates which do not require a protein carrier, such as KHL, to induce an immune response (anti-Tn IgG).

12 Claims, 14 Drawing Sheets

```
MUC6-1        MGSSHHHHHHSSGLVPRGSHMASMGGQQMGRGSSTSLVTPSTHTVIAPTHAQMATSASNHSAPTGTIPPETTLKA 76
MUC6-2        MGSSHHHHHHSSGLVPRGSHMASMGGQQMGRGSSTSLVTPSTHTVIAPTHAQMTTSASIHSMPTGTIPPETTLMA 76
Q14395 TR1    ---------------------------------STSLVTPSTHTVIAPTHAQMATSASIHSAPTGTIPPPTTLKA 42
Q14395 TR2    ---------------------------------STSLVTISTHTVITPTHPQMSTSAYIHSTPTGTIASPTTVKA 211
Q14395 TR3    ---------------------------------STSSVTPSTHTVITPTHAQMSTSASIHSTPTGTVPPLTTRMP 380
                                               *** ** ******* ******  ** ** ****  *

MUC6-1        TGSTHTAPPITPTTSGTSQAHSSFSTNKTPTSLHSHTSSTHHPEVATPSTTTIAPNPTSTRTRTPVAHTNSATSS 151
MUC6-2        TGSTHTAPLIEVATESRMSQVHSSFSTAKTSTSLLSHASSTHHP----------------------------- 119
Q14395 TR1    TGSTHTAPPITPTTSGTSQAHSSFSTNKTPTSLHSHTSSTHHPEVAPTSTTTITPNPTSTRTRTPVAHTNSATSS 117
Q14395 TR2    TRSTYTAPLMTATTRITSQAHSSISTAKTSTSLHSHASSTHHPEVTPTSTTNVTPKSTSRDTSPVTHTTSATSS 286
Q14395 TR3    TGSTRTGPPMTGTIIQTSKAHNSFSTAKTSTSLHSHASSTHHPETTPTSTTNITPKSTSAGTSPVAHTLATSS 455
              * ** ** *  *      *     * ****   ** ********

MUC6-1        RPPPPFTHSPPTGSSPESSTGPMTATSFKTTTTYPSLPQTTPLTHVPPF 203  ← SEQ ID NO:4
MUC6-2        ------------------------------------------------       SEQ ID NO:5
Q14395 TR1    RPPPPFTHSPPTGSSPFSSTGPMTATSFKTTTYPTTPSLPQTTPLTHVPPF 169  SEQ ID NO:6
Q14395 TR2    RPPTPITTHSSPTRSSPLSSTGPMTATSIKTTTTYPTPSHPQTTLTHVPPF 338  SEQ ID NO:7
Q14395 TR3    RLPTTFTTFSPPTGSSHVSSTGPMTATSSQTTTHPPPSHPQTTPLTHVP-- 505  SEQ ID NO:15
              *   *  * ************
```

FIGURE 1A

MUC6-1

MUC6-1 nucleic acid sequence (SEQ ID NO:8):
TCCACCTCCTTGGTGACTCCAAGTACTCACACAGTCATCACCCCTACCCAC
GCACAGATGGCCACATCTGCCTCCAACCACTCAGCGCCAACAGGTACCATT
CCTCCACCAACAACGCTCAAGGCCACAGGGTCCACCCACACAGCCCCACCA
ATAACGCCGACCACCAGTGGGACCAGCCAAGCCCACAGCTCATTCAGCACA
AACAAAACACCTACCTCGCTACATTCACACACTTCCTCCACACACCATCCT
GAAGTCACCCCAACTTCTACTACCACGATTACTCCCAACCCCACTAGTACA
CGCACCAGAACCCCTGTGGCCCACACCAACTCAGCCACCAGCAGCAGCAGG
CCACCACCACCCTTCACCACACACTCCCCACCTACAGGGAGCAGTCCCTTC
TCTTCCACAGGTCCCATGACGGCAACATCCTTCAAGACCACCACTACCTAT
CCAACCCCATCACTCCCTCAGACCACACCTCTCACTCATGTTCCACCTTTCTAA

MUC6-1 amino acid sequence (SEQ ID NO:9)
STSLVTPSTHTVITPTHAQMATSASNHSAPTGTIPPPTTLKATGSTHTAP
PITPTTSGTSQAHSSFSTNKTPTSLHSHTSSTHHPEVTPTSTTTITPNPTST
RTRTPVAHTNSATSSRPPPPFTTHSPPTGSSPFSSTGPMTATSFKTTTTYP
TPSLPQTTPLTHVPPF (169 aa)

Nucleic acid sequence of MUC6-1 with His-tag (SEQ ID NO:10)
ATGGGCAGCAGCCATCATCATCATCATCACAGCAGCGGCCTGGTGCCGCGC
GGCAGCCATATGGCTAGCATGACTGGTGGACAGCAAATGGGTCGCGGATCC
TCCACCTCCTTGGTGACTCCAAGTACTCACACAGTCATCACCCCTACCCAC
GCACAGATGGCCACATCTGCCTCCAACCACTCAGCGCCAACAGGTACCATT
CCTCCACCAACAACGCTCAAGGCCACAGGGTCCACCCACACAGCCCCACCA
ATAACGCCGACCACCAGTGGGACCAGCCAAGCCCACAGCTCATTCAGCACA
AACAAAACACCTACCTCGCTACATTCACACACTTCCTCCACACACCATCCT
GAAGTCACCCCAACTTCTACTACCACGATTACTCCCAACCCCACTAGTACA
CGCACCAGAACCCCTGTGGCCCACACCAACTCAGCCACCAGCAGCAGCAGG
CCACCACCACCCTTCACCACACACTCCCCACCTACAGGGAGCAGTCCCTTC
TCTTCCACAGGTCCCATGACGGCAACATCCTTCAAGACCACCACTACCTAT
CCAACCCCATCACTCCCTCAGACCACACCTCTCACTCATGTTCCACCTTTCTAA

FIGURE 10A

MUC6-2

MUC6-2 nucleic acid sequence (SEQ ID NO:11):
TCCACCTCCTTGGTGACTCCAAGTACTCACACAGTCATCACCCCTACCCAC
GCACAGATGACCACTTCTGCCTCCATCCACTCAATGCCAACAGGCACCATT
CCTCCACCGACAACGCTCATGGCCACAGGGTCCACACACACAGCCCCACTA
ATAACAGTGACCACCAGTAGGACCAGCCAAGTCCACAGCTCCTTCAGCACA
GCCAAAACCTCTACATCCCTCCTCTCCCATGCTTCCTCCACACACCATCCT
TAA

MUC6-2 amino acid sequence (SEQ ID NO:12)
STSLVTPSTHTVITPTHAQMTTSASIHSMPTGTIPPPTTLMATGSTHTAP
LITVTTSRTSQVHSSFSTAKTSTSLLSHASSTHHP (85aa)

Nucleic acid sequence of MUC6-2 with His-tag (SEQ ID NO: 13)
ATGGGCAGCAGCCATCATCATCATCATCACAGCAGCGGCCTGGTGCCGCGC
GGCAGCCATATGGCTAGCATGACTGGTGGACAGCAAATGGGTCGCGGATCC
TCCACCTCCTTGGTGACTCCAAGTACTCACACAGTCATCACCCCTACCCAC
GCACAGATGACCACTTCTGCCTCCATCCACTCAATGCCAACAGGCACCATT
CCTCCACCGACAACGCTCATGGCCACAGGGTCCACACACACAGCCCCACTA
ATAACAGTGACCACCAGTAGGACCAGCCAAGTCCACAGCTCCTTCAGCACA
GCCAAAACCTCTACATCCCTCCTCTCCCATGCTTCCTCCACACACCATCCT
TAA

FIGURE 10B

ENZYMATIC LARGE-SCALE SYNTHESIS OF MUCIN GLYCOCONJUGATES, AND IMMUNOGENIC APPLICATIONS THEREOF

CROSS-REFERENCE TO RELATED APPLICATIONS

The present application is a 371 of PCT/EB2006/002577 filed on Feb. 23, 2006 and claims the benefit of EP 06290091.5 filed Jan. 13, 2006.

FIELD OF THE INVENTION

The present invention relates to Tn-based mucin glycoconjugates, such as mucin-Tn, mucin sTn, mucin-TF glyconjugates, and to the biological, pharmaceutical, and medical applications thereof, more particularly to the immunogenic applications thereof, notably in the field of tumour treatment by palliation, prevention, therapy.

BACKGROUND OF THE INVENTION

Malignant cells selectively express on their surface molecules that have functional importance in cell adhesion, invasion and metastasis. Some of these tumour-associated structures are the result of a blockage in the glycosylation pathway. In particular, the incomplete elongation of O-glycan saccharide chains leads to the expression of shorter carbohydrate structures such as Tn, sialyl-Tn or TF antigens (Hollingsworth and Swanson 2004). The Tn antigen, defined as a GalNAc unit α-linked to a serine or threonine residue (α-GalNAc-O-Ser/Thr), is one of the most specific human tumour-associated structures. Tn is detected in about 90% of human carcinomas (Springer 1984) and its expression is correlated to carcinoma aggressiveness (Springer 1997). Moreover, under appropriate conditions, Tn is capable of inducing a strong immune response in mice and non human primates, the resulting antibodies being capable of recognizing human cancer cells (Lo-Man et al., 2001, Lo-Man et al. 2004).

This O-linked epitope is usually expressed on mucins as their carbohydrate core structure (Hollingsworth and Swanson 2004). Mucins are high molecular weight O-glycosylated proteins (50-80% of their mass is due to O-linked carbohydrate chains) that participate in protection, lubrication and acid resistance of the epithelial surface (Gendler and Spicer 1995). To date, different mucins have been identified and numbered in chronological order of their description (MUC1-MUC20) (Chen et al., 2004, Filshie et al., 1998, Gum et al. 2002, Higuchi et al. 2004, Moniaux et al., 2001, Pallesen et al., 2002, Williams et al., 2001, Yin and Lloyd 2001). Although they do not show homology of sequence, all mucins present a large region composed of variable number of tandem repeats (VNTR). These regions, usually called tandem repeats, are characterized by a high content in serine, threonine (which constitute the potential O-glycosylation sites) and proline residues.

Each organ or tissue exhibits a unique pattern of MUC gene expression (Gendler and Spicer 1995). This mucin expression profile can be modified under pathological conditions and especially during malignant transformation. Upregulation, downregulation, and de novo expression of mucin proteins have been reported in cancer epithelial cells and are thought to influence cell adhesion (Hilkens et al. 1992) and to contribute to tumour invasiveness (Segal-Eiras and Croce 1997). Moreover, these tumour-associated mucins show antigenic differences from normal mucins and are highly immunogenic and as such, they may be used as potential targets for immunotherapy (Agrawal et al. 1998, Apostolopoulos et al. 1996). In particular, MUC1 is undergoing several clinical trials as anti-cancer vaccine (Finn et al. 1995, Gilewski et al., 2000).

MUC6 was first isolated from a human stomach library (Toribara et al. 1993) and it is expressed at high levels in the normal stomach and gall bladder with weaker expression in the terminal ileum, right colon and in the endocervix (De Bolos et al., 1995, Ho et al., 1995, Reis et al. 2000, Toribara et al. 1993). MUC6 has a tandem repeat unit of 169 amino acids (507 bp each) (Toribara et al. 1993) and Southern blot analyses of the shortest MUC6 alleles indicate that they contain at least 15 repeat units (Vinall et al. 1998). Although the whole MUC6 gene was localized and identified, a full length cDNA has not been completely sequenced yet (Rousseau et al. 2004). In addition to its normal expression in gastric tissues, MUC6 has been detected in Barret adenocarcinoma and metaplasia (Guillem et al. 2000), in intestinal adenoma and carcinoma (Guillem et al. 2000), in pulmonary carcinoma (Hamamoto et al. 2005, Nishiumi et al., 2003), in colorectal polyps (Bartman et al. 1999) and in breast carcinoma (De Bolos et al. 1995, Pereira et al., 2001), while it is not expressed in the respective normal tissues. In some cases, MUC6 expression has been reported to be correlated to degrees of histopathology related to malignant potential (Bartman et al. 1999, Hamamoto et al. 2005, Nishiumi et al. 2003). We have recently shown that MUC6 is aberrantly glycosylated in MCF7 breast cancer cells since it contains the Tn antigen (Freire et al. 2005). Several studies have shown that the carbohydrate structures on mucins (including the core Tn antigen) may be essential for the definition of the tumour-associated structures (Grinstead et al., 2003, von Mensdorff-Pouilly et al., 2005). Therefore, Tn-MUC6 glycoconjugates represent attractive targets to be used in cancer immunotherapy. A specific anti-Tn antibody response should target cancer cells through the Tn antigen, which is expressed on their surface. Furthermore, the activation of mucin-specific cytotoxic T lymphocytes should be favoured through the up-take of soluble MUC6-Tn immune complexes by Fc receptors on dendritic cells (Amigorena and Bonnerot 1999).

Prior art techniques however suffer from the drawback of not enabling an easy production of mucin-Tn glycoconjugates.

Prior art mucin-Tn glycoconjugates are:
naturally-occurring glyconjugates, or
synthetic glycopeptides.

Naturally-occurring mucin-Tn glycoconjugates are obtained by isolation from a biological source (Podolsky 1985; Robbe et al. 2004). Such glycoconjugates can be obtained only in very low quantities. Their apomucin backbone is a complete apomucin protein, which bear a great number of different carbohydrate residues. The naturally-occurring mucin-Tn glycoconjugates not only contain Tn, sTn and TF antigens, but also a great number of other carbohydrate residues, the nature of which varies depending on the type, state, and status of the cell from which they originate.

The preparation of naturally-occurring antigenic glycoconjugates further relies on multi-step tedious and/or time-consuming purifications.

Other prior art mucin-Tn glycoconjugates are synthetic mucin-Tn glycopeptides. Their apomucin backbone is limited to a few amino acids.

For example, Kagan et al. 2005 discloses KHL conjugates of MUC1 or MUC2 glycopeptides. The peptide backbone of these KHL conjugates is a MUC1 or MUC2 32aa peptide, and the enzyme used to glycosylate these peptides is T2 and/or T4 N-acetylgalactosaminyltransferase(s).

Such prior art glycopeptides, when used alone, are not very efficient in inducing an immunogenic response: they require to be conjugated to a protein carrier, such as KLH, to exert their antigenic properties, if any. As a consequence, the mucin-derived glycopeptides used so far as immunogens are in fact KLH conjugates.

Other synthetic mucin glycopeptides have been described by the present inventors, in Freire et al. 2005 (Cancer Res. 65(17): 7880-7887).

Freire et al. 2005 describes the production of a MUC6-Tn glycopeptide (GTTPPPTTLK; SEQ ID NO:14), and of MUC1-Tn, MUC2-Tn, MUC5B-Tn glycopeptides. The apomucin backbone of these mucin-Tn glycoconjugates is a 9-12aa peptide (10aa for MUC6-Tn; 9aa or 11aa for MUC1-Tn; 12aa for MUC2-Tn; 11 for MUC5B-Tn; see page 7881 of Freire et al. 2005).

These mucin-Tn glycopeptides are produced:
- either by the quite expensive process of glycopeptide synthesis using a protected glycosylated building block [Fmoc-Thr($\alpha$-GalNAc(OAc)3)-OH] at the appropriate place in the peptide sequence (see the paragraph entitled "synthetic (glyco)peptides", in the "Materials and Methods" section in page 7881),
- or by enzymatic transfer of GalNAc into the apomucin peptide, wherein MCF-7 microsome extracts are used as a source of ppGalNAc-T activity, and wherein glycosylation is monitored by reverse-phase HPLC (see the paragraph entitled "Enzymatic transfer of GalNAc or Gal into MUC6 or MUC6-Tn, respectively", in the "Materials and Methods" section in page 7881; see also FIG. 1 on page 7882).

Both processes are however limited to the glycosylation of 9-12aa peptides, and do not attain semi-preparative amounts of production (mg to g).

Freire et al. 2005 does further not disclose any immunisation-related result for these MUC6-Tn, MUC1-Tn, MUC2-Tn, MUC5B-Tn glycopeptides, whether linked to a protein carrier such as KLH, or not.

In order to further develop anti-tumour vaccines based on the Tn antigen, the present inventors provide an in vitro enzymatic method for the preparation of Tn-based mucin glycoconjugates, and describe new mucin glycopolypeptides and new immunogenic compositions, which overcome the drawbacks of prior art techniques, and which can induce a highly efficient immunogenic response.

The present inventors developed an enzymatic approach, which enables the production of mucin glycoconjugates with a high Tn density in at least semi-preparative scale amounts.

Contrary to prior art synthetic glycopeptides, the mucin glycoconjugates of the invention are immunogenic, even when used in the absence of any carrier protein.

The immunogenic mucin glycoconjugates of the invention differ from the naturally-occurring glyconjugates in that their carbohydrate component does not have a heterogeneous and variable composition. The carbohydrate component of the immunogenic mucin glycoconjugates of the invention has a precise composition: each of the carbohydrate moieties that are directly O-linked to a Ser or Thr residue of the apomucin backbone is a GalNAc moiety.

To the best of the inventors' knowledge, it is the first work reporting the induction of human tumour cell-specific antibodies after immunization with a mucin derived polypeptide carrying the Tn antigen, without a protein carrier.

As a very advantageous feature, the mucin glycoconjugates produced in accordance with the present invention induce an immunogenic effect that is specific immunogenic effect: upon in vivo administration, the mucin glycoconjugates of the invention are capable of inducing antibodies, and advantageously IgG antibodies, which are capable of recognizing human tumour cells through a Tn-dependent mechanism.

SUMMARY OF THE INVENTION

In order to further develop anti-tumour vaccines based on the Tn antigen, the present inventors established an in vitro enzymatic method for the preparation of mucin glycoconjugates, and more particularly of MUC6-Tn glycoconjugates. To this end, the inventors performed the GalNAc enzymatic transfer onto the serine and threonine residues of the mucin, by using at least one UDP-N-acetylgalactosamine: polypeptide N-acetylgalactosaminyltransferase (EC 2.4.1.41, ppGalNAc-T(s)).

As an advantageous feature of the process of the present invention, SELDI-TOF (Surface-Enhanced Laser Desorption/Ionization Time-Of-Flight) mass spectrometry is used to monitor conjugation on mucin, particularly when the reaction mixture has a complex composition.

The transglycosylation method of a recombinant mucin protein according to the present invention is very convenient and effective, since 100% of the starting protein was converted into glycosylated species.

Furthermore, a high glycosylation ratio, i.e., a high Tn density, is achieved.

To the best of the inventors' knowledge, it is the first time that a Tn/sTn/TF glycosylated recombinant polypeptide, lacking any carbohydrate moiety other than Tn, sTn, or TF, is obtained in semi-preparative amounts, by the use of at least one ppGalNAc-T.

To the best of the inventors' knowledge, it is the first work reporting the induction of human tumour cell-specific antibodies after immunization with a mucin derived polypeptide carrying the Tn antigen, without a protein carrier.

As a very advantageous feature, the products which are made accessible by the present patent application are, upon in vivo administration, capable of inducing IgG antibodies, which are capable of recognizing human tumour cells through a Tn-dependent mechanism.

To the best of the inventors' knowledge, it is the first time that SELDI-TOF (Surface-Enhanced Laser Desorption/Ionization Time-Of-Flight) mass spectrometry is used to monitor conjugation on mucin, particularly when the mixture has a complex composition.

The present invention relates to the process of producing homogeneous mucin glycoconjugates, by incorporation of one or several carbohydrate moiety or moieties chosen among defined carbohydrate species (namely, Tn, sTn, TF antigens), and to the homogenous mucin glycoconjugates obtainable by this process.

The carbohydrate component of the glycoconjugates of the invention consists of at least one Tn, sTn, or TF antigen, but does not comprise any carbohydrate moiety other than Tn, sTn, TF. Therefore, the glycoconjugates of the invention are structurally much more homogeneous than naturally-occurring glyconconjugates.

The invention also relates to homogenous mucin glycopolypeptides or mucin glycoproteins (mucin-Tn, mucin-T, or mucin-sTn), the apomucin component of which is an apomucin polypeptide or protein comprising at least one mucin tandem repeat unit, or a conservative fragment or derivative thereof, as well as to the nucleic acids coding such glycopeptides, and the vectors and host cells comprising such a nucleic acid and/or expressing such a glycopolypeptide or glycoprotein. Such mucin glycopolypeptides or glycoproteins are obtainable by the process of the present invention.

The invention also relates to compositions, namely pharmaceutical compositions, drugs, immunogenic drugs, vaccines, which comprise a mucin glycoconjugate, and which do not require the presence of a protein carrier to induce an immunogenic effect.

The invention also relates to the anti-tumor applications of the mucin glycoconjugates.

BRIEF DESCRIPTION OF THE FIGURES

FIGS. 1A, 1B, 1C:

FIG. 1A. Alignment of the MUC6 cloned proteins with two known MUC6 tandem repeats.

Alignment was performed with ClustalW using the obtained predicted sequences of cloned MUC6 proteins (MUC6-1 of SEQ ID NO:4, first alignment line; and MUC6-2 of SEQ ID NO:5, second alignment line) from MCF7 breast cancer cells and with already reported MUC6 tandem repeats (TR1 and TR2 and TR3, from third to fourth alignment lines, respectively) amplified from a normal gastric library (accession number Q14395). The potential sites of O-glycosylation were determined using the NetOGlyc3.1 server and are shaded in gray. The sequences corresponding to the fusion His-tag are underlined (i.e., the first 34 N-terminal amino acids of SEQ ID NO:4 and NO:5). Identical amino acids are marked with [*].

Figure 1B:
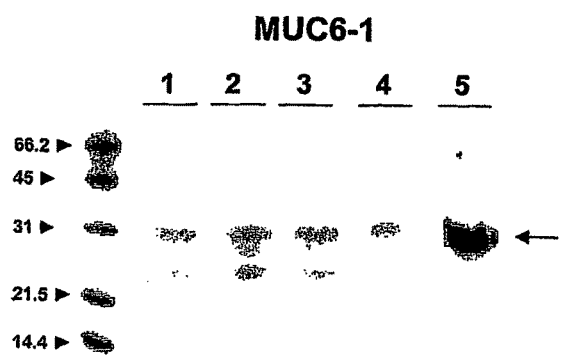

FIG. 1B. Purification of MUC6-1 recombinant protein as analyzed by SDS-PAGE.

MUC6-1 recombinant protein was purified using Ni-NTA-agarose and HPLC. Fractions were resolved by SDS-PAGE (13%) and stained with Coomassie Blue. Lanes 1-4: Ni-NTA agarose elution fractions; Lane 5: purified MUC6-1 after HPLC. Molecular markers are expressed in kDa.

Figure 1C:
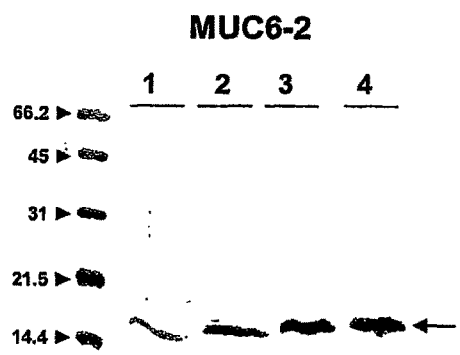

FIG. 1C. Purification of MUC6-2 recombinant protein as analyzed by SDS-PAGE.

MUC6-2 recombinant protein was purified using Ni-NTA-agarose. Fractions were resolved by SDS-PAGE (13%) and stained with Coomassie Blue. Lanes 1-4: Ni-NTA agarose elution fractions. Molecular markers are expressed in kDa.

FIGS. 2A, 2B, 2C, 2D: GalNAc transfer into MUC6 proteins and GalNAc number determination.

Figures 2A, 2B:
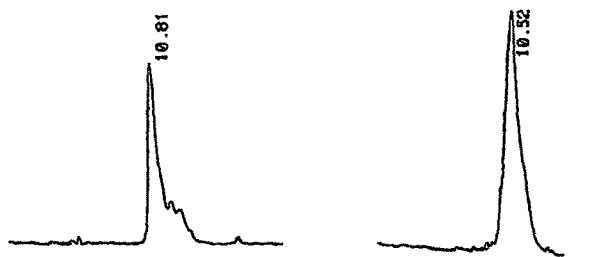

The transglycosylation reaction was performed either with MUC6-1 purified mucin (3 mg, 0.14 µmoles) and UDP-GalNAc (7.8 mg, 11.5 µmoles) using bppGalNAc-T1 (300 µg), or with MUC6-2 purified mucin (1 mg, 0.082 µmoles) and UDP-GalNAc (3.2 mg, 4.92 µmoles in two times) using MCF7 cell extracts (12 mg in two times). The MUC6-1:Tn(T1) glycoprotein was directly analyzed by HPLC (FIG. 2A). The MUC6-2:Tn(MCF7) glycoprotein was purified using Ni-NTA agarose, analyzed by HPLC (FIG. 2B). After purification by HPLC, MUC6-1:Tn(T1) (FIG. 2C) and MUC6-2:Tn(MCF7) (FIG. 2D) were analyzed by SELDI-TOF MS. Each peak is labelled with the mass/charge (m/z) value in Daltons. The corresponding number of incorporated GalNAc units is indicated in brackets.

Figure 3:
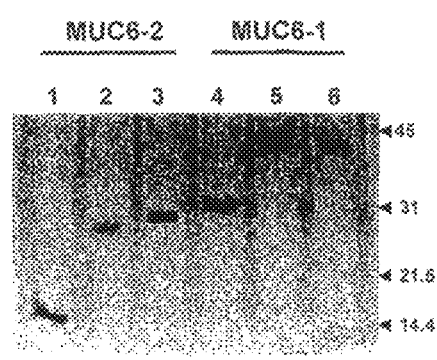

FIG. 3: SDS-PAGE of purified MUC6-1 and MUC6-2 and their glycoconjugates.

Purified glycoconjugates (0.5 µg) were separated in a 13% SDS-PAGE and stained with Coomassie blue. Lane 1: MUC6-2; Lane 2: MUC6-2:Tn(T1); Lane 3: MUC6-2:Tn (MCF7); Lane 4: MUC6-1; Lane 5: MUC6-1:Tn(T1); Lane 6: MUC6-1:Tn(MCF7). Molecular markers are expressed in kDa.

FIG. 4A, 4B, 4C, 4D, 4E: Recognition of MUC6-Tn glycoconjugates by anti-Tn mAbs by Western Blotting (A-B) and ELISA (C-E).

Glycoconjugates were separated in a 13% SDS-PAGE and transferred onto nitrocellulose sheets. An anti-His mAb (FIG. 4A) and the anti-Tn mAb 83D4 (FIG. 4B) were added, followed by an anti-mouse peroxidase conjugate and the reaction was developed with enhanced chemiluminiscence. Lane 1: MUC6-2; Lane 2: MUC6-2:Tn(T1); Lane 3: MUC6-2:Tn(MCF7); Lane 4: MUC6-1; Lane 5: MUC6-1:Tn(T1); Lane 6: MUC6-1:Tn(MCF7). Molecular markers are expressed in kDa.

The recognition of the MUC6-Tn glycoconjugates by anti-Tn monoclonal antibodies 83D4 (FIG. 4C) and MLS128 (FIG. 4D) and by a polyclonal anti-MUC6 serum (FIG. 4E) was also tested by ELISA. Asialo-ovine submaxilar mucin (aOSM, a Tn-rich mucin) was used as a control.

Figure 5A:
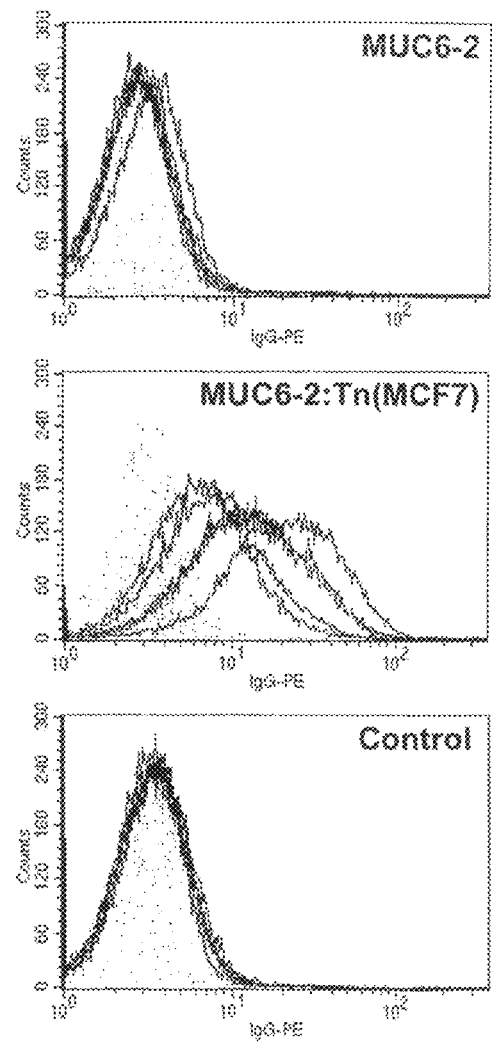
Figure 5B:
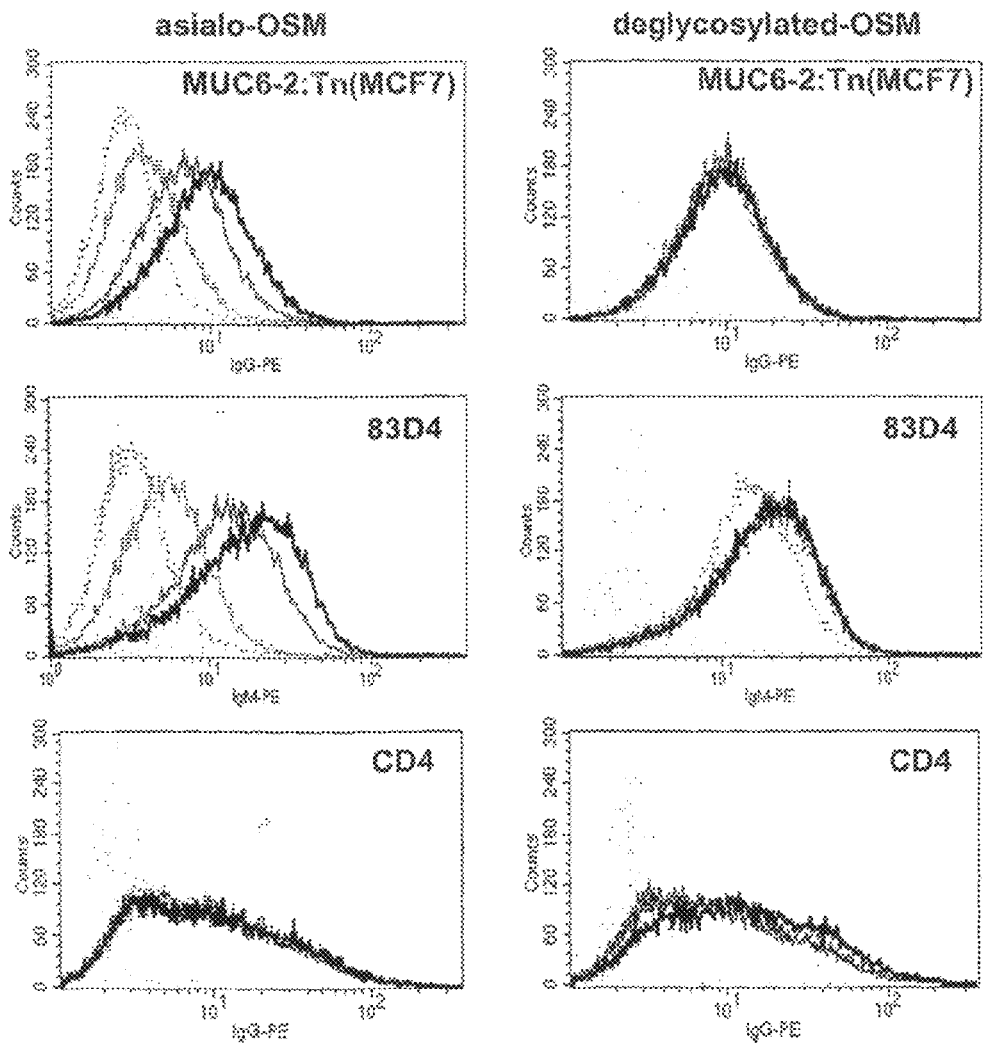

FIGS. 5A, 5B: Recognition of human Jurkat tumour cells by sera from MUC6-2:Tn(MCF7)-immunized mice.

FIG. 5A: Flow cytometry analyses were carried out on human Tn+ Jurkat tumour cells incubated with individual sera (diluted 1:500) collected from BALB/c mice (5 per group) immunized with MUC6-2, MUC6-2:Tn(MCF7) or alum plus CpG alone (control group).

FIG. 5B: For inhibition assays, cells were incubated with a pool of sera from mice immunized with MUC6-2:Tn (MCF7) together with various concentrations of asialo-OSM (Tn+ mucin) or deglycosylated-OSM (Tn-mucin). The anti-Tn IgM mAb 83D4 and an anti-CD4 IgG mAb were used as controls. Antibody binding was detected using PE-labeled antibodies specific for mouse immunoglobulin. Concentrations used for asialo-OSM or deglycosylated-OSM were: 0 µg/ml (———) 0.01 µg/ml (— — — —) 1 µg/ml (......) 100 µg/ml (- -). The results obtained with mouse sera are the result of two independent experiments.

Figure 6:
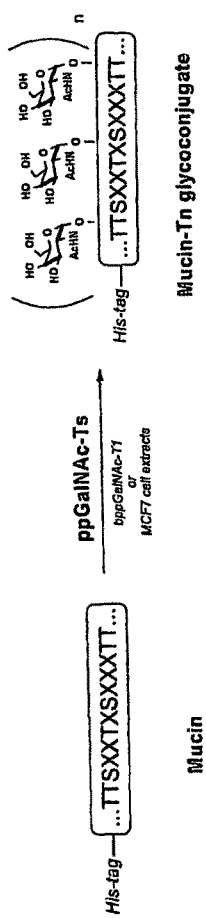

FIG. 6: Scheme of enzymatic transglycosylation of GalNAc from UDP-GalNAc to the MUC6 mucin, using either recombinant ppGalNAc-T1 or MCF-7 tumour cell extracts. FIG. 6 discloses 'TTSXXTXSXXXTT' as SEQ ID NO: 34.

FIGS. 7A-7G: SELDI-TOF MS analysis

SELDI-TOF MS analysis of the progress of the GalNAc transglycosylation on MUC6 (molecular mass, 12144.3, FIG. 7A) using ppGalNAcT1, depending on the donor amount (panels FIG. 7B-7E), and on the enzyme amount (panels E-G). Panel A served as a control for the starting material MUC6 (incubation reaction without UDP-GalNAc). The average mass/charge (m/z) values (in Daltons) are shown in each panel on the medium peak marked with an arrow. For conditions details, see Table 2 below.

Figures 7A, 7B, 7C, 7D, 7E, 7F, 7G:
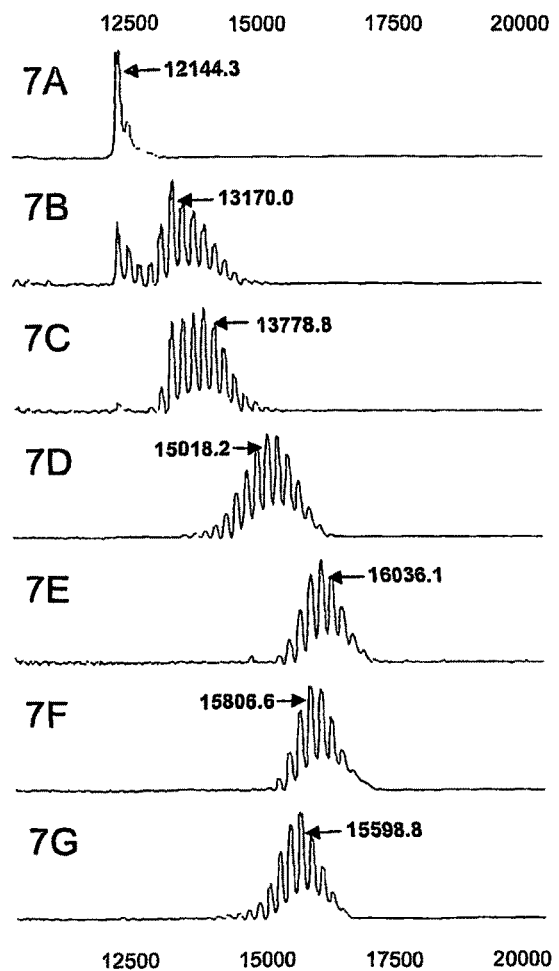
Figure 8A:
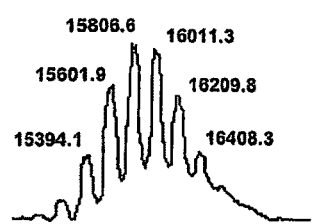
Figure 8B:
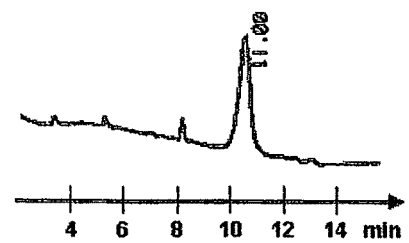

FIGS. 8A, 8B: Comparison of resolution of the analysis method on the representative experiment of FIG. 7G (1 eq of UDP-GalNAc and 1 µg of ppGalNAcT T1/10 µg of MUC6).

FIG. 8A: Enlarged SELDI-TOF mass spectrum showing the mass increment details (m/z values in daltons).

FIG. 8B: reversed-phase HPLC profile; chromatographic conditions: Waters Symmetry C18 (5 µm, 300 Å, 3.9×250 mm), flow rate of 1 mL/min, gradient with water (0.1% trifluoracetic acid)/acetonitrile (10-60%) over 30 min.

Figures 9A, 9B:
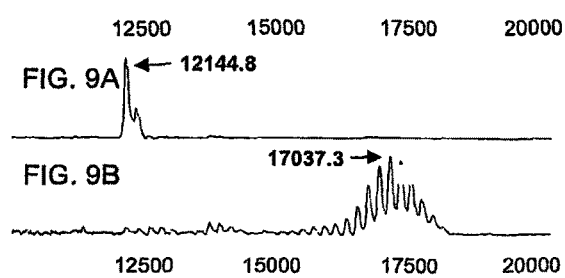

FIGS. 9A-9B:

SELDI-TOF MS analysis of the conjugation reaction using MCF-7 tumour cell extracts (FIG. 9B).

FIG. 9A served as a control for the starting material MUC6 (incubation reaction without UDP-GalNAc). The average mass/charge (m/z) values (in Daltons) are shown in both panels on the medium peak marked with an arrow. For conditions details, see Table 2 below.

FIGS. 10A and 10B show the DNA and amino acid sequences of MUC6-1 (nucleic acid sequence SEQ ID NO:8 and amino acid sequence of SEQ ID NO:9; nucleic acid sequence of MUC6-1 with His-tag=SEQ ID NO:10), and of MUC6-2 (nucleic acid sequence SEQ ID NO:11 and amino acid sequence of SEQ ID NO:12; nucleic acid sequence of MUC6-2 with His-tag=SEQ ID NO:13).

DETAILED DESCRIPTION OF THE INVENTION

In the present application, the terms <<mucin>>, <<apomucin>>, <<Tn>>, have their ordinary meaning in the field.

More particularly, a mucin is defined by the person of ordinary skill in the art skilled as a high molecular weight glycoprotein (M>$10^6$) with a high degree of O-linked glycosylation at serine and/or threonine residues. Mucin-type glycoproteins are further polymerized by S-S dependent linkage and are the major components of epithelial secretions.

Two distinctly different regions are found in naturally-occurring mature mucins:
  the amino- and carboxy-terminal regions are very lightly glycosylated, but rich in cysteines, which are likely involved in establishing disulfide linkages within and among mucin monomers,
  a large central region formed of multiple tandem repeats of 10 to 170 residues in which up to half of the amino acids are serine or threonine. This area becomes saturated with hundreds of O-linked oligosaccharides. N-linked oligosaccharides are also found on mucins, but much less abundantly.

The term "apomucin" herein refers to the protein, polypeptidic or peptidic portion of a mucin, by opposition to its carbohydrate component(s).

The Tn (T independent) antigen is a N-acetylgalactosamine carbohydrate O-linked to a Ser or Thr residue of the apomucin portion of a mucin. The Tn antigen is GalNAc-alpha1, O-Ser/Thr.

The present invention relates to products, process, and applications thereof, which are notably linked by the concept of providing Tn-based mucin glycoconjugates, more particularly mucin-Tn glycoconjugates, and glycoconjugates directly deriving therefrom by addition of organic group(s), such as mucin-T glycoconjugates and mucin-sTn glycoconjugates:
  which are not obtained by isolation from a naturally-occurring source, but are obtainable by the in vitro enzymatic synthesis process of the invention, and
  which are capable of inducing antibodies, and more particularly IgG antibodies, that recognize human tumour cells.

More particularly, the Tn-based mucin glycoconjugates of the invention are capable of inducing human tumour cell-specific anti-Tn antibodies, preferably human tumour cell-specific anti-Tn IgG and/or IgA, in the absence of any protein carrier.

To the best of the inventors' knowledge, the present invention provides the first description of means enabling the production of synthetically-produced mucin glycoconjugates which are capable of inducing such an antibody, and more particularly such an IgG production in the absence of any protein carrier.

To the best of the inventors' knowledge, it is also the first time that a Tn-based mucin glycoconjugate is obtained in semi-preparative amounts.

Hence, as an advantageous feature of the present invention, upon administration to a rodent or to a non-human primate or to a human, the Tn-based mucin glycoconjugates of the invention are able to induce antibodies, and preferably IgG and/or IgA antibodies, that recognize (i.e., bind to) a human tumor cell, such as a Jurkat cell, whereas the same but non-glycosylated mucin is not capable of such an Ig induction (see example 1 below, wherein the administration of MUC6-2:Tn(MCF7) glycoconjugate is compared to the administration of the non-glycosylated MUC6-2 protein in alum plus CpG).

The IgG and/or IgA that are induced in accordance with the present invention are directed against the glycoconjugate used for immunization (i.e., against its carbohydrate component, such as the Tn antigen, and/or against its MUC backbone).

The induced IgG and/or IgA recognize (i.e., bind to) tumor cells, and more particularly human tumour cells, such as, e.g., the human tumour cell line Jurkat (ATCC TIB-152) (see example 1 below). Preferably, said human tumour cells are breast tumoural cells, and/or pancreas tumoural cells, and/or kidney tumoural cells, and/or and/or stomach tumoural cells, and/or prostate tumoural cells, and/or ovary tumoural cells, and/or intestinal tumoural cells, and/or pulmonary tumoural cells, and/or colorectal tumoural cells.

Advantageously, this tumour recognition can be specific in the sense that an induced antibody (e.g., IgG and/or IgA) binds to a tumoural cell, but does not bind to a non-tumoural but otherwise equivalent cell.

Testing whether a given glycoconjugate induces antibodies (such as IgG and/or IgA) that recognize tumour cells is within the competence of a person of ordinary skill in the art.

For example (see, e.g., example 1 below, see also FIG. 5), the glycoconjugate to be tested can be i.p. injected into BALB/c mice. Said glycoconjugate may, e.g., be injected in alum plus CpG; control mice then only receive CpG in alun. Sera can be collected after immunization, and tested by ELISA and/or FACS for the presence of IgG directed against the glycoconjugate that has been used for immunization. Collected sera can be tested by flow cytometry for recognition of a tumour cell, such as the human tumour cell line Jurkat (ATCC TIB-152). Specific recognition can be assessed by determining that the collected sera do no recognize a non-tumoural cell, such as a breast cell, and/or a pancreas cell, and/or a kidney cell, and/or and/or stomach cell, and/or prostate cell, and/or ovary cell, and/or intestinal cell, and/or pulmonary cell, and/or colorectal cell.

If desired, the induced antibodies (e.g., IgG and/or IgA) can be purified from the collected sera.

The prior art mucin glycoconjugates require to be coupled to a protein carrier, such as KLH. They therefore have limitations regarding their application for anti-cancer immunotherapy in humans. The immune response to the carrier molecule results in a low level of the desired antibodies, as compared to the total amount of antibodies produced. This may lead to carrier-induced suppression of the immune response directed against the haptenic molecule (Schutze et al. 1985).

Contrary to these prior art glycoconjugates, the Tn-based mucin glycoconjugates of the present invention do not require to be coupled to a protein carrier, such as KLH.

Furthermore, contrary to the prior art KLH-coupled conjugates, the structure and the composition of the Tn-based mucin glycoconjugates of the present invention can be precisely determined by mass spectrometry. This feature is essential to meet the requirements of regulatory bodies for approval in humans. The present invention thereby provides compounds which are especially much more adapted to an anti-tumour vaccinal application, than the prior art glycoconjugates.

The present invention thus relates to immunogenic Tn-based mucin glycoconjugates, which, in the absence of any protein carrier, are capable of inducing antibodies, and preferably IgG and/or IgA antibodies, that recognize human tumour cells, such as a Jurkat cell. More particularly, the Tn-based mucin glycoconjugates of the invention are capable of inducing human tumour cell-specific anti-Tn antibodies, preferably human tumour cell-specific anti-Tn IgG, in the absence of any protein carrier.

The Tn-based mucin glycoconjugates of the present invention comprises at least one carbohydrate moiety, preferably a plurality of carbohydrate moieties, linked to an apomucin backbone.

At least one of these carbohydrate moieties is directly O-linked to a Ser or Thr residue of the apomucin backbone.

In the Tn-based mucin glycoconjugates of the present invention, each of the carbohydrate moieties that are directly O-linked to a Ser or Thr residue of said apomucin backbone is a GalNAc moiety.

The apomucin backbone of the Tn-based mucin glycoconjugates of the present invention advantageously is an apomucin protein, or an apomucin fragment that has retained at least one tandem repeat unit, or an apomucin sub-fragment which has retained a fragment of least 15 amino acids, preferably of at least 20 aminoacids, of the apomucin tandem repeat unit.

Preferably, said fragment or sub-fragment has retained said capacity of inducing antibodies, and more particularly IgG and/or IgA antibodies, that recognize human tumour cells, such as Jurkat cells.

Said apomucin backbone can advantageously be a conservative variant of an apomucin protein, or of an apomucin fragment or sub-fragment, said conservative variant having retained said capacity of inducing antibodies, and more particularly IgG and/or IgA antibodies, that recognize at least one human tumour cell, such as Jurkat cells.

Said apomucin backbone can advantageously be a synthetically- or recombinantly-produced apomucin backbone, which comprises at least two of apomucin proteins, and/or at least two apomucin fragments and/or sub-fragments and/or variants. Such an apomucin backbone is very advantageous, as it may lead to a Tn-based mucin glycoconjugate of the invention, which can be useful in the preventive and/or palliative and/or curative treatment of different tumours.

Each of said at least two apomucin proteins and/or fragments and/or sub-fragments and/or variants can have identical sequences, or different sequences.

Each of said at least two apomucin proteins and/or fragments and/or sub-fragments can derive from the same mucine group (e.g., MUC6, or MUC3, or MUC4, or MUC5).

Each of said at least two apomucin proteins and/or fragments and/or sub-fragments can derive from different mucin groups (e.g., MUC6 and MUC3, MUC6 and MUC4, MUC6 and MUC5, MUC3 and MUC4, MUC4 and MUC5, MUC3 and MUC5). Hence, said at least two apomucin proteins can be the apomucin of mucins that belong to different mucin groups. Said at least two apomucin fragments or sub-fragments can be the apomucin fragments or sub-fragments of mucins that belong to different mucin groups.

The apomucin backbone of the Tn-based mucin glycoconjugates of the present invention may thus comprise the amino acid sequence of:
i. at least one apomucin, and/or
ii. at least one fragment of apomucin, wherein said at least one fragment comprises at least one apomucin tandem repeat unit, and wherein said at least one fragment has retained said capacity of inducing anti-tumour antibodies, e.g., IgG and/or IgA, and/or
iii. at least one sub-fragment of apomucin, wherein said at least one sub-fragment comprises at least 15 contiguous amino acids of apomucin tandem repeat unit, and wherein said at least one sub-fragment has retained said capacity of inducing anti-tumour antibodies, e.g., IgG and/or IgA, and/or
iv. at least one conservative variant of apomucin, or of a fragment as defined ii., or of a sub-fragment as defined in iii., wherein the sequence of said at least one conservative variant has at least 70% identity with the sequence of said apomucin, or fragment, or sub-fragment, over the entire length of this protein or fragment or sub-fragment sequence, and wherein said at least one conservative variant has retained said capacity of inducing anti-tumour antibodies, e.g., IgG and/or IgA.

According to an advantageous embodiment of the present invention, the Tn-based mucin glycoconjugates of the invention is not linked to any protein carrier (i.e., an antigenic structure, typically a peptide, polypeptide or protein, or an hapten, which is capable of stimulating the immune response), such as KLH, BSA, ovalbumin, or thyroglobulin.

Said apomucin can be any apomucin or any apomucin fragment or sub-fragment that the skilled person may found appropriate.

Apomucin can be isolated from naturally-occurring mucins, or synthetized in accordance with the sequence of the apomucin, or apomucin fragment or sub-fragment of a known mucin. Hence, said apomucin, or apomucin fragment or sub-fragment, can be obtained from a naturally-occurring cell (as a cell extract, or by purification), or from a genetically engineered cell. Short length backbones may be chemically synthetised.

Up to date, twenty mucins have been identified.

Known mucins notably include: MUC1, MUC2, MUC3, MUC4, MUC5, MUC6, MUC7, MUC8, MUC9, MUC10, MUC11, MUC12, MUC13, MUC14, MUC15, MUC16, MUC17, MUC18, MUC19, MUC20.

Each of MUC1-MUC20 comprises a characteristic tandem repeat unit in its central region.

Said apomucin backbone can thus be a fragment or sub-fragment or variant of the apomucin of MUC1, MUC2, MUC3, MUC4, MUC5, MUC6, MUC7, MUC8, MUC9, MUC10, MUC11, MUC12, MUC13, MUC14, MUC15, MUC16, MUC17, MUC18, MUC19, or MUC20.

Most mucins, such as MUC1 and MUC2, have a ubiquitous expression.

In accordance with the present invention, preferred mucins therefore are those mucins which have a pattern of expression which is more particularly restricted, or specific, to tumoural cells, such as MUC6, MUC3, MUC4 and MUC5.

For example, MUC6 and MUC5 are expressed by the tumoral cells of breast tissues but are not expressed by non-tumoural breast cells, whereas MUC1 is expressed by both tumoral and non-tumoral breast cells. MUC5AC, MUC4, MUC6 are expressed by the tumoral cells of pancreas tissues but are not expressed by non-tumoural breast cells, whereas MUC1 is expressed by both tumoral and non-tumoral pancreas cells.

MUC4 is furthermore involved in apoptosis.

The respective structure of the different mucins (and more particularly, of MUC6, MUC4, MUC3, MUC5) has been described in Hollingsworth and Swanson, 2004, the content of which is herein incorporated by reference. Box 1 in page 48 of Hollingsworth and Swanson, 2004 describes the mucin domains, and more particularly the tandem repeat units.

Table 3 below shows illustrative sequences of the tandem repeat units of some mucins.

TABLE 3

Sequences of some mucin tandem repeats

| | SEQ ID NO: |
|---|---|
| MUC1 GSTAPPAHGVTSAPDTRPAP (20 aa) | 24 |
| Muc-1 DSTSSPVHSGTSSPATSAPE (20-21 aa) (mouse) | 25 |
| MUC2 PTTTPITTTTVTPTPTPTGTQT (23 AA) | 26 |
| Muc-2 PSTPSTPPPST (11-12 aa) (rat MLP) | 27 |
| MUC3 HSTPSFTSSITTTETTS (17 aa) | 28 |
| MUC4 TSSASTGHATPLPVTD (16 aa) | 29 |
| MUC5AC TTSTTSAP (8 aa) | 30 |
| MUC5B SSTPGTAHTLTVLTTTATTPTATGSTATP (29 aa) | 31 |
| MUC7 TTAAPPTPSATTPAPPSSSAPPE (23 aa) | 32 |

Said apomucin can thus be a MUC3, or MUC4, or MUC5 apomucin.

For example, said apomucin can comprise the MUC3 tandem repeat unit of SEQ ID NO: 28, or the MUC4 tandem repeat unit of SEQ ID NO:29, or the MUC5 tandem repeat unit of SEQ ID NO: 30 or 31, preferably of SEQ ID NO:30 (MUC5AC).

As a very advantageous feature of the invention, said apomucin can be a MUC6 apomucin, or a fragment or sub-fragment thereof.

Examples of genetically engineered cells which express a MUC6 apomucin fragment are the *E. coli* clones I-3491 and I-3492, which have been deposited on 10 Aug. 2005 at the CNCM in accordance with the terms of the Budapest Treaty.

Clone I-3491 expresses the apomucin polypeptide fragment, which is referred to as MUC6-1 in the examples below: it has been cloned from the breast cancer cell line MCF7, and is associated to breast cancer.

Clone I-3492 expresses the apomucin polypeptide fragment which is referred to as MUC6-2 in the examples below.

The tandem repeat unit of MUC6 is a sequence of 169 aa. Illustrative sequences of a MUC6 tandem repeat unit are the amino acid sequences of SEQ ID NO: 9, SEQ ID NO: 12, SEQ ID NO: 6, SEQ ID NO: 7, SEQ ID NO: 15 (see FIGS. 1A, 10A, 10B).

According to a preferred embodiment of the present invention, the Tn-based mucin glycoconjugates of the invention comprise at least one fragment or sub-fragment of the above-described apomucin. They may comprise several of such fragments or sub-fragments.

Such fragments or sub-fragments are, in the present invention, as defined in ii. and iii. above, i.e.:
a fragment comprises at least one apomucin tandem repeat unit, and has retained said capacity of inducing anti-tumour antibodies, e.g., IgG and/or IgA,
a sub-fragment comprises at least 15 contiguous amino acids of apomucin tandem repeat unit, and has retained said capacity of inducing anti-tumour antibodies, e.g., IgG and/or IgA.

Preferably, said at least one sub-fragment, as defined in the above iii. paragraph, comprises at least 20 contiguous amino acids, more preferably of at least 22 contiguous amino acids, most preferably of at least 25 contiguous amino acids, even more preferably of at least 30 contiguous amino acids, still more preferably of at least 35 contiguous amino acids, of said tandem repeat unit.

Said at least one sub-fragment, as defined in the above iii. paragraph, may, e.g., comprise about a half tandem repeat unit sequence (with the proviso that this half tandem repeat unit sequence is of at least 15 amino acid long).

For example, in the case of MUC6, said at least one sub-fragment may comprise at least 85 contiguous amino acids from the MUC6 tandem repeat unit. Illustrative sub-fragment sequences comprise the sequence of SEQ ID NO: 12 (MUC6-2, see FIG. 10B).

The sequence of said at least one fragment, as defined in the above iii. paragraph, may consist of a tandem repeat unit sequence of an apomucin protein, such the tandem repeat unit of an apomucin of MUC6 (for example, SEQ ID NO:9, SEQ ID NO:6, SEQ ID NO:7, or SEQ ID NO:15), MUC3 (for example, SEQ ID NO: 28), MUC4 (for example, SEQ ID NO: 29), or MUC5 (for example, SEQ ID NO: 30 or 31, preferably SEQ ID NO: 30).

Advantageously, the sequence of said apomucin backbone is, or derives from a MUC6 apomucine.

More particularly, the sequence of said apomucin backbone can be:
a. a MUC6 apomucine, or
b. is a polypeptide or a protein, which:
   α. comprises at least one tandem repeat unit of a MUC6 apomucin, or
   β. comprises at least one conservative fragment of a MUC6 apomucin tandem repeat unit, wherein said conservative fragment has retained a number of Ser and Thr residues of at least 30, or
c. is a conservative amino acid variant of a MUC6 apomucine (as defined in a.), or of a polypeptide or protein as defined in b., wherein the sequence of said conservative variant has an identity of at least 70% with:
   the sequence of said at least one tandem repeat unit contained in said MUC6 tandem repeat unit-containing apomucin fragment (as defined in α.), over the entire length of this tandem repeat unit sequence, or
   with the sequence of said conservative fragment of MUC6 apomucin tandem repeat unit (as defined in β.), over the entire length of this conservative fragment sequence,
and
   said conservative variant sequence has retained a number of Ser and Thr residues of at least 30.

Preferably said minimal number of Ser and Thr residues contained in the is MUC6 or MUC6-derived apomucin polypeptide backbone is of at least 32, more preferably of at least 35, still more preferably of at least 37, most preferably of at least 40, even more preferably of at least 45.

The Tn-based mucin glycoconjugates of the present invention can have any desired % of O-glycosylation.

When the apomucin backbone to be glycosylated has a small number of Ser and Thr residues, very high GalNAc transfer rate can be attained, such as e.g. at least 80%, preferably at least 85%, more preferably at least 90%, most preferably at least 95%, still more preferably at least 98%, even more preferably at least 99%, e.g., 100%.

An advantageous feature of the present invention is that it describes a process that enables to attain high Tn density on complex polypeptide or protein backbones, such as those deriving from MUC6. In the MUC6 tandem repeat unit, which is of 169 amino acids, the total number of Ser and Thr residues (=potential O-glycosylation sites) is of about 83. The present invention enables to achieve high glycosylation rates on polypeptide or protein back as complex as a MUC6 or MUC6-derived backbone (see example 1 below).

In accordance with the present invention, at least 40% of the total number of Ser and Thr residues contained in the apomucin backbone, such as a MUC6 or MUC6-derived backbone, can be directly O-linked to at least one N-acetylgalactosamine (GalNAc).

In other words, the overall density of Tn antigens contained in a Tn-based mucin glycoconjugate of the present invention, such as a MUC6 or MUC6-derived glycoconjugate of the invention, is (or the carbohydrate density of the glycopolypeptides of the invention) of at least 40%.

More preferably, said total number of GalNAc O-linked Ser and Thr residues is of at least 41%, still more preferably of at least 42%, even more preferably of at least 43%, most preferably of at least 45%.

Said total number of GalNAc O-linked Ser and Thr residues can even be of at least 50%, preferably of least 51%, more preferably of least 52%, even more preferably of at least 53%, still even more preferably of at least 55%, most preferably of at least 57%.

The process of the present invention further enables the production of Tn-based mucin glycoconjugates, such as MUC6 or MUC6-derived glycoconjugates, wherein the total number of GalNAc O-linked Ser and Thr residues is of at least 58%, more preferably of at least 60%, even more preferably of at least 61%, still even more preferably of at least 62%, most preferably of at least 65%.

For example, the MUC6 or MUC6-derived mucin-Tn glycopolypeptides described in the examples below have a Tn density (=% of GalNAc O-linked Ser and Thr residues) of 42% [MUC6-2:Tn(T1)], 54% [MUC6-2:Tn(MCF7)], 58% [MUC6-1:Tn(MCF7)], and of 64% [MUC6-1:Tn(T1)].

The immunogenic Tn-based mucin glycoconjugate of the invention preferably comprise at least one CTL epitope in their apomucin backbone.

Advantageously, said apomucin fragment or sub-fragment which may be comprised in the apomucin backbone of an Tn-based mucin glycoconjugate of the invention has retained at least CTL epitope.

In accordance with the present invention, preferred tandem repeat unit fragments are those which have retained at least one CTL epitope.

CTL epitopes can be identified by the skilled person, e.g., using a prediction site.

In the MUC6-1 sequence of SEQ ID NO:4 shown in FIG. 1A (MUC6-1 with His tag), CTL epitopes notably include the following sequences:
from position 38 to position 46 (LVTPSTHTV; SEQ ID NO:16);
from position 66 to position 74 (GTIPPPTTL; SEQ ID NO:17);
from position 73 to position 81 (TLKATGSTH; SEQ ID NO:18);
from position 67 to position 75 (TIPPPTTLK; SEQ ID NO:19);
from position 120 to position 128 (EVTPTSTTT; SEQ ID NO:20);
from position 40 to position 48 (TPSTHTVIT; SEQ ID NO:21);
from position 68 to position 76 (IPPPTTLKA; SEQ ID NO:22);
from position 31 to position 39 (GRGSSTSLV; SEQ ID NO:23).

In the MUC6-1 sequence without His tag (SEQ ID NO:9 shown in FIG. 10A), as well as in the MUC6 sequences shown in SEQ ID NO: 6, SEQ ID NO: 7 and SEQ ID NO: 15 in FIG. 1A, these CTL epitopes correspond to the sequences extending:
from position 4 to position 12;
from position 32 to position 40;
from position 39 to position 47;
from position 33 to position 41;
from position 86 to position 94;
from position 6 to position 14;
from position 34 to position 40;
of SEQ ID NO: 6, SEQ ID NO: 7 and SEQ ID NO: 15, respectively.

In the MUC6-2 sequence of SEQ ID NO:5, shown in FIG. 1A (MUC6-2 with His tag), CTL epitopes notably include the following sequences:
from position 38 to position 46 (LVTPSTHTV; SEQ ID NO:16);
from position 66 to position 74 (GTIPPPTTL; SEQ ID NO:17);
from position 73 to position 81 (TLKATGSTH; SEQ ID NO:18);
from position 67 to position 75 (TIPPPTTLK; SEQ ID NO:19);
from position 40 to position 48 (TPSTHTVIT; SEQ ID NO:21);
from position 68 to position 76 (IPPPTTLKA; SEQ ID NO:22);
from position 31 to position 39 (GRGSSTSLV; SEQ ID NO:23).

In the MUC6-2 sequence without His tag (SEQ ID NO:12 shown in FIG. 10B), these CTL epitopes correspond to the sequences extending:
from position 4 to position 12;
from position 32 to position 40;
from position 39 to position 47;
from position 33 to position 41;
from position 6 to position 14;
from position 34 to position 40.

Other preferred mucin glycoconjugates of the present invention are those which bear at least one CTL neo-epitope. Indeed, glycoproteins, glycopolypeptides and glycopeptides can link one or several MHC Class II molecule, and induce CTL which are carbohydrate-specific (Haurum et al. 1994, Aurum et al. 1999, Abdel-Motal et al. 1996, Apostolopoulos et al. 2003, Glithero et al. 1999, Speir et al. 1999, Xu et al. 2004).

The Tn-based mucin glycoconjugates of the present invention may further comprise at least one entity, which can be an organic entity, such as a protein or a polypeptide or a peptide or a carbohydrate, but which is other than an apomucin or an apomucin fragment (as herein defined) or a Tn antigen.

Such another entity may indeed be found useful, and chosen by the person of ordinary skill in the art, notably to help in the production of said Tn-based mucin glycoconjugate, and/or to help in its detection in a sample, and/or to increase its biological effects.

Said Tn-based mucin glycoconjugate may for example comprise at least one entity which can be useful for its purification from a sample, such as a His-tag sequence (e.g., the 34 first N-terminal amino acids of SEQ ID NO:4 or SEQ ID NO:5 (see FIG. 1A)).

Said Tn-based mucin glycoconjugate may for example comprise at least one entity which is helpful in the detection of a glycoconjugate in a sample, and notably in biological sample.

Said Tn-based mucin glycoconjugate may for example comprise at least one purification and/or detection tag.

Said Tn-based mucin glycoconjugate may for example comprise at least one entity which can be useful for its secretion from a host cell, such as a signal peptide.

To increase its biological effects, the mucin glycoconjugates of the invention may for example comprise at least one entity which is an anti-tumour agent, and/or which helps in targeting a tumour cell.

The mucin glycoconjugates of the invention can have a linear peptide backbone, a cyclic peptide backbone, a multivalent peptide backbone. They can comprise lipids (as palmitoyl residus), lysine dendrimers (such as MAG backbone, see EP 969 873).

Although the present invention enables the production of mucin glycoconjugates which are antigenic in the absence of any protein carrier, the skilled person may of course, in certain circumstances, found appropriate or helpful to couple or otherwise associate the Tn-based mucin glycoconjugate with such a protein carrier. Such carrier-coupled glycoconjugates therefore are included within the scope of the present invention.

The preferred embodiment of the invention however is that the Tn-based mucin glycoconjugate of the invention do not comprise any protein carrier, such as KLH.

The present invention also relates to those mucin glycoconjugates which are derivable from the Tn-based mucin glycoconjugates of the invention, by addition of at least one other carbohydrate group other than said directly O-linked GalNAc.

The Tn-based mucin glycoconjugate may more particularly comprise at least one carbohydrate moiety linked to at least one of said directly O-linked GalNAc moieties.

Such derivable mucin glycoconjugates notably include mucin-sTn glycoconjugates (such as mucin-sTn glycopolypeptide conjugates), and mucin-T glycoconjugates (such as mucin-T glycopolypeptide conjugates).

Indeed, the sialyl transferase may elongate the Tn antigen with a sialyl group to form the sialosyl-Tn, or sialyl-Tn, (sTn) antigen (NeuAc-alpha(2-6)-GalNAc-alpha-O-Ser/Thr). The expression of this antigen is frequently induced during the process of carcinogenesis.

The T (or TF, Thomsen-Friedenreich) antigen is defined by a mucin disaccharide that is O-linked to proteins:Galbeta1,3-GalNAc-alpha1, O-Ser/Thr. The Tn (T negative) antigen is GalNAc-alpha1, O-Ser/Thr. Thus, beta1,3-galactosylation of Tn generates the T epitope.

Hence, the invention provides direct access to mucin-T glycoconjugates, which are obtainable by (at least one) beta1,3-galactosylation of a herein described Tn-based mucin glycoconjugate.

Said at least one other carbohydrate group may thus comprise, or be:
  a sialyl group (sialyl-Tn), such as Neu5Ac (N-acetylneuramic acid), Neu5Gc (N-glycolylneuramic acid), KDN, or their direct derivatives such as Neu2en5Ac, Neu2en5Gc, KDN2en; or
  Gal.

Said at least one other carbohydrate group may thus comprise, or be:
  a sialyl group (sialyl-Tn), such as Neu5Ac (N-acetylneuramic acid), Neu5Gc (N-glycolylneuramic acid), KDN, or their direct derivatives such as Neu2en5Ac, Neu2en5Gc, KDN2en;
  N-acetylmannosamine (ManNAc),
  Gal, or
  any carbohydrate group that the person of ordinary skill in the art may found appropriate, notably for anti-tumour applications, such as, e.g., a glycolipid, notably a glycosidic antigen, including acidic glycolipid such as, for example, gangliosides GD2, GD3 and GM3 (melanoma) and neutral glycolipids such as, for example, the Lewis.sup.y (Le.sup.y) (breast, prostate, ovary) and the Globo H (breast, prostate, ovary) antigens.

The present invention more particularly relates to Tn-based mucin glycoconjugates, wherein said at least one GalNAc-linked carbohydrate moiety is a GalNAc moiety, a syalyl group, or a galactose moiety.

The Tn-based mucin glycoconjugates of the invention may comprise more than one apomucin, or apomucin fragment or sub-fragment in their backbone. Such Tn-based mucin glycoconjugates have the advantage of being adapted to the preventive and/or palliative and/or curative treatment of different tumour pathologies.

The Tn-based mucin glycoconjugates of the invention may thus have an apomucin backbone, which comprise the sequence of:
  at least two apomucins, and/or
  at least two fragments as herein defined (see ii. above), and/or
  at least two sub-fragments as herein defined in iii., and/or
  at least one apomucin, and at least one fragment as herein defined in ii., and/or
  at least one apomucin, and at least one sub-fragment as herein defined in iii., and/or
  at least one fragment as herein defined in ii., and at least one sub-fragment as herein defined in iii.

Advantageously, each of the two elements contained in said apomucin backbone are from different apomucins, preferably from apomucins of different mucin groups (e.g., MUC6 and MUC3, MUC6 and MUC4, MUC6 and MUC5, MUC3 and MUC4, MUC3 and MUC5, MUC4 and MUC5).

Each of said at least two fragments, and/or of said least two sub-fragments, and/or of said at least one fragment and at least one sub-fragment, contained in said apomucin backbone, preferably is a fragment, or sub-fragment, of a different apomucin.

Advantageously, said apomucin backbone comprises the amino acid sequence of at least two apomucins proteins, and/or of at least two fragments as herein defined in ii., and/or at least two sub-fragments as herein defined in iii.

Preferably, each of said at least two fragments or sub-fragments is a fragment, or sub-fragment, of a different apomucin, most preferably of apomucins of different mucin groups (e.g., MUC6 and MUC3, MUC6 and MUC4, MUC6 and MUC5, MUC3 and MUC4, MUC3 and MUC5, MUC4 and MUC5).

According to a very advanteous embodiment, the sequence of each of said at least two fragments is the tandem repeat unit sequence of an apomucin protein.

The present invention also provides a process for the production of Tn-based mucin glycoconjugates.

The process of the invention is an in vitro enzymatic synthesis.

The invention thus relates to a process of in vitro production of a Tn-based mucin glycoconjugate, which enables the production of Tn-based mucin glycoconjugates which, in the absence of any protein carrier, can induce antibody, and more particularly IgG and/or IgA antibodies, that recognize human tumour cells, such as Jurkat cells. As a very advantageous feature, the process of the invention enables the production of such Tn-based mucin glycoconjugates in at least semi-preparative scale amounts (more than 100 micrograms, preferably in mg amounts).

The process of the invention comprises in vitro transferring at least one N-acetylgalactosamine (GalNAc) on a Ser or Thr residue contained in a protein or polypeptide or peptide acceptor, wherein said in vitro transfer is a transfer that is performed enzymatically using at least one UDP-N-acetylgalactosamine: polypeptide N-acetylgalactosaminyltransferase (ppGalNAc-T).

The process of the invention does not require any intact cell activity; it does not require the presence of any intact cell.

The result of the implementation of the process of the invention is that each of the carbohydrate moieties that are directly O-linked to a Ser or Thr residue of said apomucin backbone is a GalNAc moiety.

Said protein or polypeptide or peptide acceptor advantageously is an apomucin backbone, as herein defined, i.e., an apomucin protein, or an apomucin fragment that has retained at least one tandem repeat unit, or an apomucin sub-fragment which has retained a fragment of least 15 amino acids, preferably of at least 20 aminoacids, of the apomucin tandem repeat unit.

Preferably, said fragment or sub-fragment is a conservative fragment that has retained said capacity of inducing antibodies, and more particularly IgG and/or IgA antibodies, that recognize human tumour cells, such as Jurkat cells.

Said protein or polypeptide or peptide acceptor can advantageously be a conservative variant of an apomucin protein, or of an apomucin fragment or sub-fragment, said conservative variant having retained said capacity of inducing antibodies, and more particularly IgG and/or IgA antibodies, that recognize at least one human tumour cell, such as Jurkat cells.

Said protein or polypeptide or peptide acceptor can advantageously be a synthetically- or recombinantly-produced apomucin backbone, which comprises at least two of apomucin proteins, and/or at least two apomucin fragments and/or sub-fragments and/or variants.

Each of said at least two apomucin proteins and/or fragments and/or sub-fragments and/or variants can have identical sequences, or different sequences.

Each of said at least two apomucin proteins and/or fragments and/or sub-fragments can derive from the same mucine group (e.g., MUC6, or MUC3, or MUC4, or MUC5).

Each of said at least two apomucin proteins and/or fragments and/or sub-fragments can derive from different mucin groups (e.g., MUC6 and MUC3, MUC6 and MUC4, MUC6 and MUC5, MUC3 and MUC4, MUC4 and MUC5, MUC3 and MUC5). Hence, said at least two apomucin proteins can be the apomucin of mucins that belong to different mucin groups. Said at least two apomucin fragments or sub-fragments can be the apomucin fragments or sub-fragments of mucins that belong to different mucin groups.

The protein or polypeptide or peptide backbone used as protein or polypeptide or peptide acceptor in the process of the invention has the same features as the protein or polypeptide or peptide backbone of the Tn-based mucin glycoconjugates of the present invention.

The features given for the products of the invention apply to the process of the invention.

To date, fifteen ppGalNAc-Ts have been identified in mammals, and functional profiles of each member of the family have been established showing that these enzymes have not only different substrate specificities, but also specific tissue-expression patterns (Cheng et al., 2004, Ten Hagen et al. 2003).

In accordance with the present invention, appropriate ppGalNAc-Ts notably include those which are involved in tumour pathologies.

Advantageous ppGalNAc-Ts comprise those tumour-related ppGalNAc-Ts which are selected from ppGalNAc-T1, ppGalNAc-T2, ppGalNAc-T3, ppGalNAc-T6, ppGalNAc-T7, and ppGalNAc-T13.

Very advantageous ppGalNAc-Ts comprise those tumour-related ppGalNAc-Ts which are selected from ppGalNAc-T1, ppGalNAc-T3, ppGalNAc-T6, ppGalNAc-T7, and ppGalNAc-T13.

Said at least one ppGalNAc-T can be provided in pure or purified form, or in the form of a cellular extract.

Said at least one ppGalNAc-T can be provided by providing an enzyme-containing extract of a cancer cell, such as a microsome extract, or a protein extract, or by providing ppGalNAc-T(s) purified from such an extract.

Any cancer cell that the skilled person may find appropriate can be used. Preferred cancer cells include breast cancer cells, such as the breast cancer cell line MCF7 (ATCC number HTB-22), colon, lung, ovary, prostate cancer cells.

Said at least one ppGalNAc-T can be a recombinantly-produced ppGalNAc-T, e.g. a ppGalNAc-T obtainable by expression by, and purification from, genetically engineered yeast cell, such as a *Pichia pastoris* strain (e.g., the KM71H strain available from Invitrogen), or insect cells infected by baculovirus vectors.

Said in vitro transfer is advantageously performed under conditions of ppGalNAc-T quantity, UDP-GalNAc quantity, and incubation time, which are favourable to a maximal number of GalNAc transfers. Indeed, those mucin glycoconjugates which have the highest glycosylation levels are likely to give the highest immune response, and therefore are very advantageous active agents for the production of vaccines, and notably of anti-tumour vaccines.

For an apomucin backbone as complex as the one of a MUC6 apomucin (which has a tandem repeat unit of 169 aa), such optimal conditions notably include the provision of said at least one ppGalNAc-T by providing a quantity of at least 0.1 microgram of said ppGalNAc-T, or of cell extract containing such a ppGalNAc-T, per 10 micrograms of said apomucin.

Said quantity of ppGalNAc-T, or of cell extract containing such a ppGalNAc-T, per 10 micrograms of said apomucin, preferably is of at least 0.2 microgram, most preferably of at least 0.3 microgram, more preferably of at least 0.4 microgram, still more preferably of at least 0.5 microgram, for example less than 2 micrograms, preferably less than 1.5 micrograms, most preferably not higher than 1 microgram (any value range resulting from the combinations of these values being herein explicitly encompassed).

If desired, several ppGalNAc-Ts (preferably a mixture thereof) can be used.

For an apomucin backbone as complex as the one of the MUC6 apomucin, such optimal conditions may notably include the provision of said at least one GalNAc in a molar equivalent amount of 0.5 to 2 equivalents of UDP-GalNAc, as compared to potential O-glycosylation sites.

The incubation time is dependent of the amounts of the reactants (apomucin or apomucin fragment, ppGalNAc-T(s), UDG-GalNAc).

The incubation times can be of at least 10 hours, preferably of at least 20 h, e.g. of at least 24 h.

Reactants, such as UDP-GalNAc and ppGalNAc-T(s), and can be further added during the course of the reaction, e.g. after 24 h of reaction.

Said GalNAc transfer can be monitored by any means known to the skilled person, such as e.g. HPLC.

According to a very advantageous feature of the present invention, said GalNAc transfer is monitored by SELDI-TOF mass spectrometry.

SELDI-TOF is Surface-Enhanced Laser Desorption/Ionization Time-Of-Flight. SELDI-TOF mass spectrometry is especially advantageous, when the reaction mixture has a complex composition, which is notably the case when one or several of the reactants are provided as a biological extract, such as a cell-extract containing one or several ppGalNAc-T(s).

To the best of the inventors' knowledge, it is the first time that SELDI-TOF (Surface-Enhanced Laser Desorption/Ionization Time-Of-Flight) mass spectrometry is used to monitor conjugation on mucin, particularly when the mixture has a complex composition.

The present application thus also relates to the use of SELDI-TOF mass spectrometry to monitor the course of a GalNAc bioconjugation in a mixture containing a cell extract.

When the GalNAc transfers have been achieved to the desired level, the obtained Tn-based mucin glycoconjugates can be purified from the reaction mixture, if desired and/or required.

Purification can e.g. be performed on an affinity column (e.g., if the glycoconjugate has been his-tagged, adsorption on a Ni-NTA-agarose (Qiagen, Hilden, Germany)), and/or by reverse HPLC.

For example, the resulting glycoconjugates can be purified using Ni-NTA-agarose (Qiagen, Hilden, Germany) and then subjected to reversed phase HPLC using a Perkin-Elmer pump system with an UV detector at 230 nm. The column can be a Symmetry 300™ C18 (5 µm, 300 Å, 3.9×250 mm) (Waters, France). Elution can be carried out with a linear gradient of 10-60% acetonitrile in 0.1% trifluoracetic acid in water at a flow rate of 1 mL/min (over 30 min). The peak can then be collected and lyophilized. The glycoproteins thus obtained may then be characterized by AAA and mass spectrometry.

As illustrated by examples 1 and 2 below, in all assays performed by the inventors on MUC6 apomucin fragment under optimal GalNAc conditions, the starting polypeptide was totally converted into glycoconjugates (100%). The process of the invention therefore has very high production efficiency.

To the best of the inventors' knowledge, if is the first time that a Tn-glycosylated recombinant polypeptide is obtained in semi-preparative amounts, by the use of at least one ppGalNAc-T.

The process of the invention can be conducted up to any desired GalNAc transfer %. As above-mentioned, SELDI-TOF mass spectrometry is preferably used to monitor the conjugation reactions.

An advantageous feature of the process of the invention is that it enables the production of Tn-based mucin glycoconjugates which have a high overall density of Tn antigens (=high carbohydrate density).

When the backbone to be glycosylated has a small number of Ser and Thr residues, very high GalNAc transfer rate can of course be attained, such as e.g. at least 80%, preferably at least 85%, more preferably at least 90%, most preferably at least 95%, still more preferably at least 98%, even more preferably at least 99%, e.g. 100%.

An advantageous feature of the present invention is that it further enables to attain high Tn density on complex polypeptide backbones, such as those deriving from MUC6. In the MUC6 tandem repeat unit, the total number of Ser and Thr residues (=potential O-glycosylation sites) is of about 83.

In accordance with the present invention, at least 40% of the total number of Ser and Thr residues contained in an apomucin backbone, such as a MUC6 a MUC6-derived apomucin backbone, can be directly O-linked to at least one N-acetylgalactosamine (GalNAc).

More preferably, the number of Ser and Thr residues that are directly O-linked to a GalNAc moiety is of at least 41%, still more preferably of at least 42%, even more preferably of at least 43%, most preferably of at least 45%.

Said number of GalNAc O-linked Ser and Thr residues can even be of at least 50% of the total number of Ser and Thr residues, preferably of least 51%, more preferably of least 52%, even more preferably of at least 53%, still even more preferably of at least 54%, most preferably of at least 57%.

The process of the present invention further enables the production of Tn-based mucin glycoconjugates, wherein the number of GalNAc O-linked Ser and Thr residues is of at least 58% of the total number of Ser and Thr residues, more preferably of at least 60%, even more preferably of at least 61%, still even more preferably of at least 62%, most preferably of at least 64%.

Each % range which results from the combination of two different values from the above-mentioned GalNAc % values is explicitly encompassed by the present invention.

The present application also relates to the Tn-based mucin glycoconjugates obtainable by the process the invention.

The present invention also relates to any nucleic acid coding for the apomucin of a Tn-based mucin glycoconjugate of the present invention.

Said coding sequence can for example code for the apomucin polypeptide fragment of SEQ ID NO:6, SEQ ID NO:7, SEQ ID NO:15 (see FIG. 1A).

Said coding sequence can for example code for the apomucin polypeptide fragment of SEQ ID NO:9 or NO:12 (see FIGS. 10A and 10B). Said coding sequence can the be the sequence of SEQ ID NO:8 or NO:11 (see FIG. 10).

Said nucleic acid may further comprise a stop codon at the 3'-terminal end of said Tn-based mucin glycoconjugate coding sequence.

Said nucleic acid further comprises a sequence coding for a purification and/or detection tag, such as a His-tag. For example, said nucleic acid can code for the His-tagged apomucin polypeptide fragment of SEQ ID NO:4 or NO:5 (see FIG. 1A); it may for example be the sequence of SEQ ID NO:10 or SEQ ID NO:13 (see FIGS. 10A and 10B).

Said nucleic acid may further comprise a leader sequence (coding for a signal peptide).

The present invention also relates to any vector comprising at least one nucleic acid of the present invention, such as e.g. a plasmid comprising an origin of replication, and at least one nucleic acid of the present invention.

Preferably, said vector is an expression vector.

The present invention also relates to any genetically engineered host cell which expresses a Tn-based mucin glycoconjugate according to the present invention, as a result of said genetic engineering, and/or which has been genetically engineered to comprise at least one nucleic acid according to the present invention and/or at least one vector according to the present invention. Such a host cell can be a transfected host cell, an infected host cell, a transformed host cell.

Such a host cell may any host cell that the skilled person may find appropriate. It can e.g. be a eukaryotic cell (e.g. yeast, or mammalian cell), or a prokaryotic cell (e.g. E. coli), or insect cell infected by baculovirus.

Advantageous host cells of the invention notably comprise the E. coli host cells deposited under deposit number CNCM I-3491 and under deposit number CNCM I-3492, on the 10 Aug. 2005, in accordance with the terms of the Budapest Treaty.

The present invention thus also relates to any Tn-based glycoconjugate expressed by a host cell according to the present invention, such as the Tn-based mucin glycoconjugate of SEQ ID NO:9 or NO:12 (see FIGS. 10A and 10B).

The present invention also relates to any compound which comprises at least one Tn-based mucin glycoconjugate, and at least one entity other than a mucin, an apomucin, an apomucin fragment (as herein defined), a Tn antigen, or a carbohydrate.

The present invention more particularly relates to a soluble immune complex, which comprises:
  at least one Tn-based mucin glycoconjugate according to the invention, and
  at least one immunoglobulin structure, or at least one immunoglobulin fragment which is a Fc fragment, a Fv fragment, a Fab fragment, a F(ab)'2 fragment, a light chain, or a heavy chain.

The apomucin fragment contained in said immune complex can advantageously be a fragment of the apomucin of MUC6, and notably a polypeptide fragment of MUC6 apomucin (soluble MUC6-Tn immune complex).

Upon in vivo administration, the mucin glycoconjugates, which are made accessible by the present invention have the advantageous feature of being capable of inducing antibodies, and more particularly IgG antibodies, which are capable of recognizing human tumour cells through a Tn-dependent mechanism.

IgG induction is a particularly useful feature when immunogenic composition or immunogenic drug, and vaccines are contemplated, as antibody-dependent cellular cytotoxicity (ADCC) is highly useful to obtain an efficient immune response, notably against tumoral or pre-tumoral cells. Hence, the feature of being capable of IgG induction is a very advantageous feature of the mucin glycoconjugates, and more particularly the mucin glycopolypeptide conjugates, of the present invention.

As another very advantageous feature, the mucin glycoconjugates of the present invention are also capable of such an antibody (including IgG) induction, in the absence of any protein carrier. The immunogenicity efficiency is therefore improved, compared to prior art mucin glycoconjugates.

Also the absence of any required protein carrier is very advantageous, notably when administration to human beings is contemplated.

The present application thus relates to the prevention and/or alleviation and/or treatment of a condition or disease in which tumour cells are involved, such as notably a cancerous or pre-cancerous state or condition.

A prevention and/or alleviation and/or treatment method of the invention comprises the administration of a product of the invention to a patient in need thereof.

The present invention also relates to adjuvant, compositions, pharmaceutical compositions, immunogenic compositions, drugs, immunogenic drugs, and vaccines, which are intended for such a prevention and/or alleviation and/or treatment.

The adjuvant, compositions, pharmaceutical compositions, immunogenic compositions, drugs, immunogenic drugs, and vaccines of the present invention comprise at least one product of the invention, namely at least one among the following elements:
  the Tn-based mucin glycoconjugates according to the invention,
  the nucleic acids according to the invention,
  the vectors according to the invention,
  the genetically engineered host cells according to the invention,
  the soluble immune complexes according to the invention,
  the Tn-based mucin glycoconjugates according to the invention.

The adjuvant, compositions, pharmaceutical compositions, immunogenic compositions, drugs, immunogenic drugs, and vaccines, of the present invention may further comprise at least one pharmaceutically and/or physiologically acceptable vehicle (carrier, diluent, excipient, additive, pH adjuster, emulsifier or dispersing agent, preservative, surfactant, gelling agent, as well as buffering and other stabilizing and solubilizing agent, etc.).

Appropriate pharmaceutically acceptable vehicles and formulations include all known pharmaceutically acceptable vehicles and formulations, such as those described in "Remington: The Science and Practice of Pharmacy", 20$^{th}$ edition, Mack Publishing Co.; and "Pharmaceutical Dosage Forms and Drug Delivery Systems", Ansel, Popovich and Allen Jr., Lippincott Williams and Wilkins.

In general, the nature of the carrier will depend on the particular mode of administration being employed. For instance, parenteral formulations usually comprise, in addition to the one or more contrast agents, injectable fluids that include pharmaceutically and physiologically acceptable fluids, including water, physiological saline, balanced salt solutions, buffers, aqueous dextrose, glycerol, ethanol, sesame oil, combinations thereof, or the like as a vehicle. The medium also may contain conventional pharmaceutical adjunct materials such as, for example, pharmaceutically acceptable salts to adjust the osmotic pressure, buffers, preservatives and the like. The carrier and composition can be sterile, and the formulation suits the mode of administration.

For solid compositions (e.g., powder, pill, tablet, or capsule forms), conventional nontoxic solid carriers can include, for example, pharmaceutical grades of mannitol, lactose, starch, sodium saccharine, cellulose, magnesium carbonate, or magnesium stearate. In addition to biologically-neutral carriers, pharmaceutical compositions to be administered can contain minor amounts of auxiliary substances, such as wetting or emulsifying agents, preservatives, and pH buffering agents and the like, for example sodium acetate or sorbitan monolaurate.

The composition can be a liquid solution, suspension, emulsion, tablet, pill, capsule, sustained release formulation, or powder. The composition can be formulated with traditional binders and carriers, such as triglycerides.

The present application more particularly relates to immunogenic compositions, immunogenic drugs, and vaccines of the present invention. The immunogenic compositions, immunogenic drugs, and vaccines of the present can be used in therapy and/or prophylaxis.

The term vaccine thus herein encompasses therapeutic, as well as prophylactic vaccine.

The immunogenic compositions, immunogenic drugs, and vaccines of the present invention, can be intended for the treatment and/or prevention and/or palliation of a tumour or pre-tumour state or condition.

The present invention thus notably relates to anti-tumour immunogenic compositions, anti-tumour immunogenic drugs, and anti-tumour vaccines of the present invention.

In the present invention, the term "tumor" or "tumour" is meant as encompassing "cancer".

Such tumour states or conditions notably comprise any type of carcinoma, adenoma, adenocarcinoma, metaplasia, or any type of cancer, and more particularly those which affect or can affect the lung, the breast, the intestinal tract, and still more particularly those which affect or can affect a human being, such as:

Barret adenocarcinoma, intestinal carcinoma and adenoma, pulmonary carcinoma, colorectal polyps, breast carcinoma, pancreas, kidney, stomach, prostate, ovary, cholangiocarcinome.

ATCC is American Type Culture Collection ATCC; P.O. Box 1549; Manassas, Va. 20108; U.S.A.

CNCM is Collection Nationale de Cultures de Microorganismes; Institut Pasteur; 25, rue du Docteur Roux; F-75724 PARIS CEDEX 15; France.

The term "comprising", which is synonymous with "including" or "containing", is open-ended, and does not exclude additional, unrecited element(s), ingredient(s) or method step(s), whereas the term "consisting of" is a closed term, which excludes any additional element, step, or ingredient which is not explicitly recited.

The term "essentially consisting of" is a partially open term, which does not exclude additional, unrecited element(s), step(s), or ingredient(s), as long as these additional element(s), step(s) or ingredient(s) do not materially affect the basic and novel properties of the invention.

The term "comprising" (or "comprise(s)") hence includes the term "consisting of" ("consist(s) of"), as well as the term "essentially consisting of" ("essentially consist(s) of"). Accordingly, the term "comprising" (or "comprise(s)") is, in the present application, meant as more particularly encompassing the term "consisting of" ("consist(s) of"), and the term "essentially consisting of" ("essentially consist(s) of").

Each of the relevant disclosures of all references cited herein is specifically incorporated by reference. The following examples are offered by way of illustration, and not by way of limitation.

EXAMPLES

Example 1

Enzymatic Large-Scale Synthesis of MUC6-Tn Glycoconjugates for Anti-Tumour Vaccination Abstract In cancer, mucins are aberrantly O-glycosylated and consequently, they express tumour-associated antigens such as the Tn determinant (α-GalNAc-O-Ser/Thr). They also exhibit a different pattern of expression as compared to normal tissues. In particular, MUC6, which is normally expressed only in gastric tissues, has been detected in intestinal, pulmonary, colorectal and breast carcinomas. Recently, our laboratory has shown that the MCF7 breast cancer cell line expresses MUC6-Tn glycoproteins in vivo. Cancer-associated mucins show antigenic differences from normal mucins and, as such, they may be used as potential targets for immunotherapy. In order to develop anti-cancer vaccines based on the Tn antigen, we prepared several MUC6-Tn glycoconjugates. To this end, we performed the GalNAc enzymatic transfer to two recombinant MUC6 proteins expressed in E. coli by using UDP-N-acetylgalactosamine: polypeptide N-acetylgalactosaminyltransferases (ppGalNAc-Ts), which catalyze in vivo the Tn antigen synthesis. We used either a mixture of ppGalNAc-Ts from MCF7 breast cancer cell extracts or a recombinant ppGalNAc-T1. In both cases, we achieved the synthesis of MUC6-Tn glycoconjugates at a semi-preparative scale (mg amounts). These glycoproteins displayed a high level of Tn antigens, although the overall density depends on both enzyme source and protein acceptor. These MUC6-Tn glycoconjugates were recognized by two anti-Tn monoclonal antibodies which are specific for human cancer cells. Moreover, the MUC6-Tn glycoconjugate glycosylated using MCF7 extracts as the ppGalNAc-T source was able to induce IgG antibodies that recognized a human tumour cell line. In conclusion, the production in large amounts of MUC6 with tumour-relevant glycoforms hold considerable promise for developing effective anti-cancer vaccines and further studies of their immunological properties are warranted.

Introduction

In the present example, we used either a recombinant ppGalNAc-T1 or a microsome extract from MCF7 breast cancer cells containing ppGalNAc-Ts, in order to better mimic the glycosylation of cancer cells.

We show that the in vitro enzymatic method of the invention for the preparation of MUC6-Tn glycoconjugates (in vitro GalNAc enzymatic transfer onto the serine and threonine residues of the mucin, by using ppGalNAc-Ts) is very efficient and allowed the preparation of semi-preparative quantities of different MUC6-Tn glycoproteins with high carbohydrate density. The resulting MUC6 glycoconjugates were shown to be antigenic as judged by the recognition by two anti-Tn monoclonal antibodies (mAbs) specific for human cancer cells. Moreover, the MUC6-Tn glycoconjugate glycosylated using MCF7 extracts as the ppGalNAc-T source, was able to induce IgG antibodies that recognized a human tumour cell line.

Results

MUC6 Recombinant Protein Production in E. coli and Enzymatic Synthesis of Tn-Expressing MUC6 Mucins In order to obtain semi-preparative amounts of Tn-expressing MUC6 glycoproteins, we designed two recombinant MUC6 proteins, cloned from the MCF7 breast cancer cell line, and containing:

either a whole tandem repeat unit (MUC6-1; protein sequence of SEQ ID NO:4, wherein the first N-terminal 34 aa are a His-tag sequence, and the 169 following aa are the sequence of a MUC6 tandem repeat unit), or a half tandem repeat (MUC6-2; protein sequence of SEQ ID NO:5, wherein the first N-terminal 34 aa are a His-tag sequence, and the 85 following aa are the sequence of a MUC6 half tandem repeat unit); see FIG. 1A.

These two different constructs were selected in order to study the glycosylation of two related proteins of different sizes, with different number of potential O-glycosylation sites (85 for MUC6-1 and 48 for MUC6-2). Slight amino acids changes were detected between the two cloned MUC6 cDNAs and the reported MUC6 cDNAs (SEQ ID NO:6 and NO:7 faire concorder avec TR1 et TR2) cloned from gastric tissues (Toribara et al. 1993) (see alignment in FIG. 1A). This could be attributed to the high polymorphism found in mucin tandem repeats.

MUC6-1 and MUC6-2 polypeptides were expressed in *E. coli* and purified using Ni-NTA-agarose (FIGS. 1B and C).

An *E. coli* clone producing MUC6-1 and an *E. coli* clone expressing MUC6-2 have been deposited on Aug. 10, 2005 at the CNCM under accession numbers I-3491 and I-3492, respectively.

For MUC6-1, one additional step of purification using a C18 column was necessary (FIG. 1B). As a result, purified MUC6-1 and MUC6-2 proteins were obtained with a purity level >95%, as estimated by HPLC, at a yield of 2 mg and 3.4 mg of protein per liter of culture, respectively.

These purified mucin proteins (MUC6-1 or MUC6-2) were subjected to in vitro transglycosylation reactions from UDP-GalNAc by using either a recombinant bppGalNAc-T1, or a MCF7 cell extract (FIG. 6). The reactions were performed at analytical scale under different conditions (incubation time, UDP-GalNAc equivalents and enzyme quantity). The course of the transfer was monitored by High Performance Liquid Chromatography (HPLC) and Surface-Enhanced Laser Desorption/Ionization Time-Of-Flight Mass Spectrometry (SELDI-TOF MS) and the reaction parameters giving the highest Tn density were selected (see example 2 below). These conditions (see Table 1 below) were used to perform the semi-preparative scale synthesis of MUC6-Tn (~0.3-3 mg).

TABLE 1

Conditions used for transglycosylation assays and characteristics of the resulting glycoconjugates

| | UDP-GalNAc equivalents [1] | Enzyme or extract amount/μg of mucin | Obtained quantity (mg) | Product yield (%) [2] | Experimental Molecular mass (Da) [3] | Average GalNAc number [3] | Tn (% w.) | Glycosylated sites (%) [4] |
|---|---|---|---|---|---|---|---|---|
| MUC6-1 | — | — | — | — | 20833.7 | — | — | — |
| MUC6-1: Tn(T1) | 1 eq: 24 hs/37° C. | 0.1 μg | 2.5 | 59 | 31778.5 | 54 | 34 | 64 |
| MUC6-1: Tn(MCF7) | (0.5 eq: 24 h/37° C.) × 2 [5] | (6 μg) × 2 [5] | 0.35 | 25 | 30718.5 | 49 | 32 | 58 |
| MUC6-2 | — | — | — | — | 12157.5 | — | — | — |
| MUC6-2: Tn(T1) | 1 eq: 24 h/37° C. | 0.1 μg | 2.5 | 69 | 16220.5 | 20 | 25 | 42 |
| MUC6-2: Tn(MCF7) | (0.5 eq: 24 h/37° C.) × 2 [5] | (6 μg) × 2 [5] | 0.5 | 34 | 17473.4 | 26 | 30 | 54 |

Figure 2C:
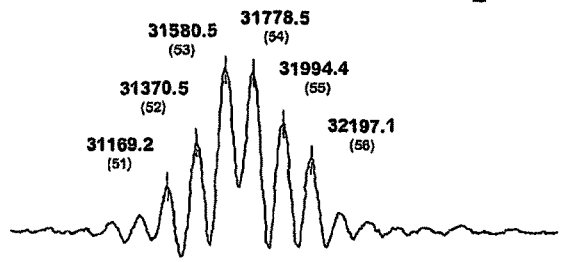
Figure 2D:
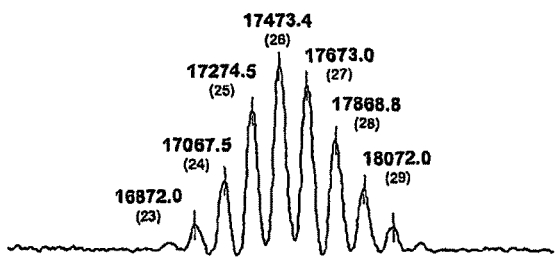

In the above table 1:
[1] The equivalent amount is expressed as compared to the total potential O-glycosylation sites (i.e., total serine and threonine residues)
[2] Isolated product yields refer to the obtained yield after the glycosylation reaction and purification of the resulting glycoprotein. MUC6-Tn glycoconjugates were tested for the endotoxin levels, and found to be lower than 2 EU/mg of glycoprotein in all cases
[3] The average molecular mass and GalNAc number of the glycoconjugate were calculated from the medium peak
[4] The % of obtained glycosylated sites was calculated taking into account the obtained GalNAc number for each glycoconjugate as compared to the total number of serine and threonine residues in the proteins (85 for MUC6-1 and 48 for MUC6-2) (100%)
[5] The same quantity of UDP-GalNAc equivalents and enzyme were added at the beginning of the reaction and then at 24 hrs A maximal GalNAc-transfer was achieved since purified MUC6-Tn glycoconjugates were not further glycosylated after being subjected again to the same glycosylation reaction conditions. The resulting glycoproteins were analyzed by HPLC (FIGS. 2A and 2B), purified, and then characterized by SELDI-TOF MS (FIGS. 2C and 2D). In all assays, the starting protein was totally converted into glycoconjugates. The SELDI-TOF MS profiles showed different GalNAc glycosylation levels of the protein (major peak±3 GalNAc) (FIGS. 2C and 2D). A similar polydispersity was observed on the crude mixtures and on the purified glycoconjugates, independently of the protein acceptor and of the enzyme source used.

Physico-Chemical Characterization of the Synthesized Glycoconjugates

Four different MUC6 glycoconjugates were synthesized by this enzymatic transglycosylation and purified by Ni-NTA agarose and HPLC. Then, they were subjected to SDS-PAGE analysis (FIG. 3) confirming the presence of purified glycoproteins at the expected molecular weights. The MUC6 glycoproteins presented different Tn content, depending on the mucin backbone and on the different ppGalNAc-T source used (Table I). When the MCF7 breast cancer cell extract was used, an average of 54-58% of potential O-glycosylation sites was glycosylated, representing 30-32% of the total molecular mass, independently of the mucin used as acceptor. A different Tn density was obtained when the mucin proteins were glycosylated by the purified bppGalNAc-T1. MUC6-2 was less glycosylated (20 GalNAc, representing 42% of total O-glycosylation sites). On the other hand, MUC6-1 was much more glycosylated by bppGalNAc-T1 since 64% of the potential O-glycosylated sites were glycosylated (54 GalNAc).

MUC6-Tn Glycoconjugates are Recognized by Anti-Tn mAbs

The MUC6 glycoproteins were identified by Western Blotting using anti-Tn (83D4) and anti-His mAbs (FIG. 4).

Figure 4A:
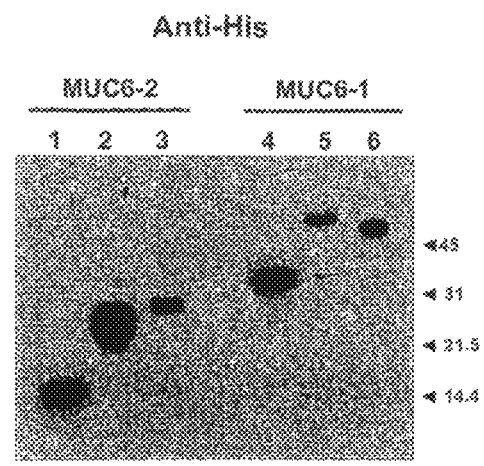
Figure 4B:
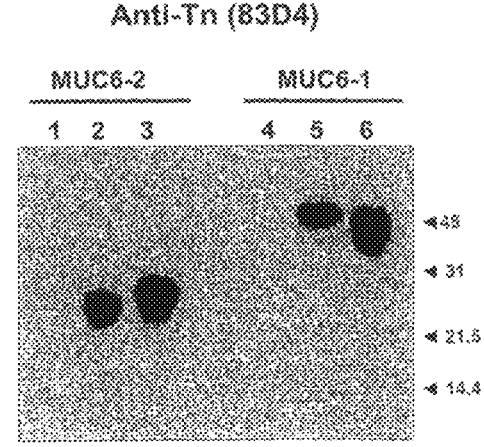

As expected, the anti-His mAb recognized all MUC6 proteins (including the non-glycosylated MUC6) (FIG. 4A). On the contrary, the anti-Tn mAb 83D4 only recognized the MUC6-Tn glycoconjugates (FIG. 4B).

Figure 4C:
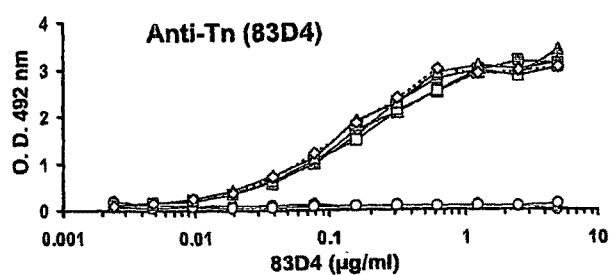
Figure 4D:
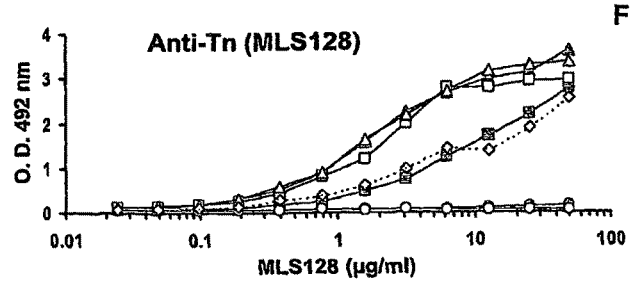
Figure 4E:
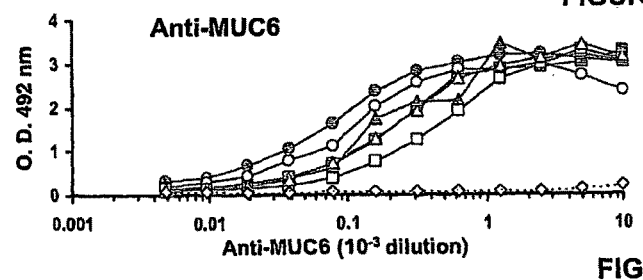

The antigenicity of these MUC6 glycoconjugates was analyzed by ELISA using two anti-Tn mAbs raised against human cancer cells (MLS128 and 83D4) and a polyclonal anti-MUC6 serum. FIG. 4C-D shows that both anti-Tn mAbs, although at different rates, recognized the MUC6-Tn glycoconjugates, whereas the corresponding non-glycosylated MUC6 proteins were not recognized. The anti-Tn mAb 83D4 similarly recognized MUC6-1 and MUC6-2 glycoconjugates (FIG. 4C) while MLS128 showed less reactivity with the MUC6-2:Tn(T1) glycoconjugate, which was the one with the lowest Tn density (FIG. 4D). All glyco- and non-glycosylated MUC6 proteins were differently recognized by the anti-MUC6 serum (FIG. 4E). The non-glycosylated MUC6 proteins were slightly more reactive than the MUC6-Tn glycoconjugates, probably due to the lack of accessibility to the protein backbone in highly glycosylated proteins.

MUC6-2:Tn(MCF7) Glycoconjugate Induces Antibodies that Recognize Tumour Cells

The immunogenicity of one of the MUC6-Tn glycoconjugates was studied. BALB/c mice were immunized with the MUC6-2:Tn(MCF7) glycoconjugate, or with the non-glycosylated MUC6-2 protein in alum plus CpG, and sera were tested for their capacity of recognizing the human tumour cell line Jurkat (FIG. 5). Control mice received only CpG in alum. It is worth noting that all MUC6 glycoproteins showed very low levels of endotoxins (<2 EU/mg of protein). Immunization with the MUC6-2:Tn(MCF7) glycoconjugate, but not with the non-glycosylated MUC6-2 protein, induced IgG antibodies that recognized the Jurkat human tumour cell line (FIG. 5A).

In order to confirm that these antibodies recognized the Tn antigen on these cells, we carried out inhibition assays using either asialo-OSM (carrying the Tn antigen) or deglycosylated-OSM. As shown in FIG. 5B, only asialo-OSM inhibited the recognition of the Jurkat cells by sera obtained after immunization with MUC6-2:Tn(MCF7) and by the anti-Tn mAb 83D4 (used as control). In contrast, the binding of an anti-CD4 antibody to Jurkat cells was not affected in either of the two cases (FIG. 5B). These experiments clearly show that MUC6-2:Tn(MCF7) can induce anti-Tn antibodies that recognize Tn+ tumour cells.

Discussion

The aim of cancer immunotherapy is to elicit protective immunity against cancer cells without causing collateral autoimmune damage. One approach is based on the induction of tumour-specific immune responses by cancer-associated antigens. To this end, mucins can be used as immunogens in vaccines designed to elicit therapeutic anti-tumour immunity.

Cancer-associated changes occur not only in mucin protein expression between normal and abnormal tissues, but also in the pattern of O-glycosylation that distinguishes cancer mucins from normal mucins. Indeed, mucins are normally highly glycosylated and thus, the antigenic peptide core is physically inaccessible to the immune system, and particularly to antibodies. However, in tumour cells, they present cancer-associated truncation of O-linked carbohydrate chains creating the tumour-specific TF, Tn and sialyl-Tn antigens (Hollingsworth and Swanson 2004). This suggests that such glycosylated mucins can be used as targets for treatment of specific cancers.

Various vaccines based on the Tn structure have been developed and tested in preclinical or clinical models. Desialylated ovine submaxillary mucin (expressing high Tn levels) (Singhal et al., 1991) and Tn protein conjugates (Kuduk et al. 1998; Longenecker et al., 1987; US 2003/0083235 A1; Toyokuni et al. 1994; U.S. Pat. No. 5,660,834) induced high Tn-specific antibody titers in mice resulting in protection against tumour challenge. In humans, desialylated red blood cells (rich in Tn and T antigens) allowed a protection against recurrence of advanced breast cancer (Springer et al., 1993). More recently, a clinical trial with a Tn-protein conjugate resulted in an anti-tumour effect as determined by a to decline in the PSA slope (Slovin et al. 2003). Our laboratory also reported the preparation of a fully synthetic vaccine based on the Tn antigen, the MAG for Multiple Antigenic Glycopeptide (Bay et al. 1997). MAG: Tn vaccines are capable of inducing, in mice and in non-human primates, strong tumour-specific anti-Tn antibodies that can mediate antibody-dependent cell cytotoxicity against human tumour cells (Lo-Man et al. 2004). However, large scale preparation of such conjugates is limited by the complexity of the whole synthesis process. To further extend the scope of our approach to clinical trials, we propose to enzymatically attach the Tn antigen to a mucin core protein. In the present example, we chose the MUC6 mucin which is aberrantly expressed in different cancers and may constitute a target antigen itself. Indeed, MUC6 has been detected in intestinal, pulmonary, colonic and mammary adenocarcinomas while it is not expressed by the respective normal tissues (Bartman et al., 1999, De Bolos et al. 1995, Guillem et al. 2000, Hamamoto et al. 2005, Nishiumi et al. 2003, Pereira et al., 2001). Furthermore, our preliminary data suggest that MUC6 carries the Tn antigen in MCF7 breast cancer cells (Freire et al. 2005). In the present example, we describe the enzymatic synthesis of Tn-expressing MUC6 glycoconjugates. In order to produce high amounts of MUC6-Tn glycoconjugates, we performed the GalNAc transfer to a recombinant MUC6 protein expressed in *E. coli* by using ppGalNAc-Ts. This large family of enzymes catalyzes in vivo the linking of a GalNAc residue to serine or threonine (i.e., the synthesis of the Tn antigen). To date, fifteen ppGalNAc-Ts have been identified in mammals, and functional profiles of each member of the family have been established showing that these enzymes have not only different substrate specificities, but also specific tissue-expression patterns (Cheng et al. 2004, Ten Hagen et al. 2003).

Glycosyltransferases have been extensively used as tools to perform transglycosylation reactions since they are an attractive alternative to the total chemical synthesis of large glycosyl amino acids (Marcaurelle and Bertozzi 2002). The synthesis of glycopeptides and glycoconjugates with O-linked glycans has already been reported, especially for the sialyl-Tn (George et al., 2001) and sialyl-T antigens (Ajisaka and Miyasato 2000, George et al. 2001). ppGalNAc-Ts have also been used successfully for the in vitro synthesis of glycopeptides. Most of the studies aimed at investigating the specificities of these different enzymes (either recombinant or from cell extracts) for various peptide substrates from MUC1 (Takeuchi et al. 2002) or MUC2 (Irimura et al. 1999, Kato et al. 2001), and they were performed at the analytical scale (0.1-10 µg range). Interestingly, however, recombinant ppGalNAc-T2 and -T4 allowed the preparation of MUC1-Tn glycopeptides which were used for immunization purposes (Kagan et al. 2005, Sorensen et al. 2005).

In the present example, we used either ppGalNAc-Ts from cancer cell extracts or purified recombinant bovine ppGalNAc-T1 to achieve the maximal GalNAc transfer to the serine and threonine residues of a MUC6 recombinant protein. These two ppGalNAc-T sources were chosen for two reasons.

On the one hand, breast cancer cell extracts were used in order to better mimic the in vivo O-glycosylation sites of MUC6 in cancer cells.

On the other hand, the recombinant bppGalNAc-T1 has a very broad specificity and the in vitro glycosylation assays using a purified recombinant protein are expected to give more reproducible results and to allow easier purification. Indeed, the product yield obtained using both ppGalNAc-T sources was different, being higher when using the recombinant bppGalNAc-T1 (59-69% for bppGalNAc-T1 versus 25-34% for MCF7 extracts). This difference is due to an additional step needed to purify the MUC6-Tn glycoconjugates from the reaction mixture containing MCF7 cell extract.

Although significant progress has recently been made in the synthesis of glycoconjugates, the access to this type of macromolecules remains very difficult, particularly when large quantities are required. To our knowledge, this is the first time that a Tn-glycosylated recombinant protein is obtained in semi-preparative amounts, by the use of ppGalNAc-Ts. By selecting the best conditions for maximal GalNAc transfer, we obtained MUC6 glycoconjugates carrying high densities of Tn antigen. These different Tn densities (54 GalNAc for MUC6-1:Tn(T1), 49 GalNAc for MUC6-1:Tn (MCF7), 20 GalNAc for MUC6-2:Tn(T1) and 26 GalNAc for MUC6-2:Tn(MCF7)) are the result of independent and reproducible experiments. Depending on the enzyme source, we produced glycoconjugates with different Tn levels. This could be explained by the specificity of ppGalNAc-Ts (not all threonine and serine residues are recognized by one ppGalNAc-T) (Ten Hagen et al. 2003).

We also studied the glycosylation of two MUC6 recombinant proteins of different size (203 aa for MUC6-1, and 119 aa for MUC6-2), in order to evaluate if the GalNAc transfer is influenced by the length of the protein. When using a recombinant bppGalNAc-T1, we obtained an average of 54 and 20 incorporated GalNAc residues out of 85 and 48 potential O-glycosylation sites (total number of Thr and Ser residues) for MUC6-1 and MUC6-2 respectively, representing 64% and 43% of O-glycosylation sites approximately. Structural studies would help to determine whether these distinct glycosylation rates are due to a lack of accessibility of bppGalNAc-T1 for the acceptor sites in the mucin protein.

Of primary importance in the design of vaccines against cancer is that the antigen in the vaccine mimics the antigen on the tumour. In order to synthesize structures close to the native Tn clusters present in cancer cells, we also performed the GalNAc transfer using MCF7 breast cancer cell extracts, which may express various ppGalNAc-T isoforms, as already shown on other human cancer cell lines (Freire et al. 2005, Mandel et al. 1999, Marcos et al., 2003). In this case, similar GalNAc density was obtained, being 49 for MUC6-1 and 26 for MUC6-2, representing 58% and 54%, respectively, of potential O-glycosylation sites. Thus, the degree of glycosylation obtained with the purified recombinant bppGalNAc-T1 and MCF7 cell extracts is different and, surprisingly, the Tn density is not necessarily higher in the latter case. This could be explained by the presence of different ppGalNAc-Ts in the cell extract, which act in a coordinate and sequential manner, and may contribute positively or negatively to the overall glycosylation of the protein.

Most of anti-Tn antibodies raised against cancer cells or tissues recognize groups of adjacent Tn epitopes usually called Tn clusters. Indeed, 83D4 and MLS128 anti-Tn mAbs require the presence of at least two consecutive Tn residues for substrate recognition (Nakada et al. 1993, Osinaga et al., 2000). Taking into account that 2/3 of the Thr and Ser residues in MUC6-1 and MUC6-2 are arranged in clusters, it is highly probable that most of the Tn antigens will be presented, at least, as clusters of two Tn. The potential relevance of the MUC6-Tn glycoconjugates for tumour immunotherapy is evidenced by the analysis of their antigenicity. Indeed, the Tn antigen on MUC6 was recognized by Tn-specific monoclonal antibodies such as MLS128 and 83D4 and confirms the presence of Tn clusters. Analyses of the O-glycosylation in MUC6 proteins in order to determine the glycosylation sites in the different MUC6-Tn glycoconjugates are in progress.

As an example, we have also shown that one of the MUC6-Tn glycoconjugates is immunogenic. Indeed, MUC6-2:Tn(MCF7) induced IgG antibodies in mice, which were capable of recognizing human tumour cells through a Tn-dependent mechanism. To our knowledge, this is the first work reporting the induction of human tumour cell-specific antibodies after immunization with a mucin derived protein carrying the Tn antigen, without a protein carrier. Indeed, the mucin-derived glycopeptides used so far as immunogens are KLH conjugates (Kagan et al. 2005, Sorensen et al. 2005).

In conclusion, the transglycosylation method of a recombinant mucin protein presented here is very convenient and effective, since 100% of the starting protein was converted into glycosylated species.

Furthermore, a high glycosylation ratio is achieved. The ability to produce recombinant MUC6 with tumour-relevant glycoforms in large amounts is unique and will be extremely valuable for preclinical, immunological and tumour-protection studies. The anti-tumour potency of MUC6-Tn glycoconjugates is currently underway.

Materials and Methods

MUC6 Cloning and Expression in *E. coli*

A cDNA clone containing one tandem repeat of human MUC6 was isolated from total cDNA of MCF7 breast cancer cells by RT-PCR and cloned into pGem®-T (Promega, France). The PCR products were designed to encode one tandem repeat of human MUC6 (MUC6-1, 169 amino acids) or a half tandem repeat (MUC6-2, 85 amino acids) that were amplified with Pfu DNA polymerase and the primers:

MUC6-F, 5'-cgggatccTCCACCTCCTTGGTGACT-3' (SEQ ID NO:1), and

MUC6-1R (for MUC6-1) of sequence 5'-ggaagcttTTAGAAAGGTGGAACGTG-3' (SEQ ID NO:2), or MUC6-2R (for MUC6-2) of sequence 5'-ggaagcttATTAGGATGGTGTGTGGA-3' (SEQ ID NO:3), (lowercase characters indicate restriction sites for BamHI and HindIII in the forward and reverse primers, respectively).

Following digestion with BamHI and HindIII, each product was cloned into the pET28a(+) vector (Novagen, Fontenay-sous-Bois, France), so as to encode for a protein carrying a six-histidine tail (SEQ ID NO: 33) at the N-terminus. *E. coli* DH5α (ATCC 53868) transformants were selected on LB plates containing 50 μg/ml kanamycin and the positive clones were confirmed by PCR and sequencing.

Plasmids were purified from selected clones and used to transform *E. coli* BLi5 chemically competent cells (Novagen, Fontenay-sous-Bois, France). The recombinants were expressed in *E. coli* Bli5 by induction with 1 mM IPTG and purified over Ni2+-nitriloacetic acid columns under denaturing conditions according to the manufacturer's (Qiagen, Germany) instructions. MUC6-1 protein was further purified by HPLC using a Perkin-Elmer pump system with an UV detector at 230 nm. The column was a Symmetry 300 ™ C18 (5 µm, 300 Å, 3.9×250 mm) (Waters, France). Elution was carried out with a linear gradient of 10-60% acetonitrile in 0.1% trifluoracetic acid in water at a flow rate of 1 mL/min (over 30 min). The MUC6 proteins were characterized by amino acid analysis (AAA) and SELDI-TOF MS. These analyses, together with a N-terminal sequencing, showed that both proteins lack the N-terminal methionine residue.

Breast Cancer Cell Line Extract

Breast cancer cell line MCF7 (ATCC number HTB-22) was grown to 90% confluence in Dulbecco's modified Eagle's medium (Life Technologies, Inc., Cergy Pontoise, France) with 10% fetal bovine serum, 1 mM pyruvate, 2 mM glutamine and 5% CO2 at 37° C. After trypsinization, cells were washed three times with phosphate-buffered saline (PBS), resuspended in 250 mM sucrose and homogenized. Cells were then centrifuged at 3,000 g for 10 min at 4° C. The resulting supernatant was again centrifuged at 100,000 g for 1 h at 4° C. The pellet was resuspended in 0.1 M imidazole pH 7.2 and 0.1% Triton™ X-100. The cell extract was aliquoted and stored at −80° C. Protein concentration was determined by the BCA method (Sigma Chemical Co., St Louis, Mo.).

Recombinant Bovine ppGalNAc-T1

A soluble form of the bovine ppGalNAc-T1 (bppGalNAc-T1) was expressed in the yeast *Pichia pastoris* KM71H strain (Invitrogen, Cergy Pontoise, France) and purified from the culture supernatant (see Duclos et al. 2004).

The cDNA coding region for the soluble form of the bppGalNAc-T1 (from amino acids 52 to 559) was introduced in 3' of the .alpha.-factor sequence signal coding region of a pPICZ.alpha.A expression vector (Invitrogen) modified to introduce a N-terminal 6His-tag and a C-terminal FLAG®-tag. The KM71H strain was made competent using the *Pichia* EasyComp™ kit (Invitrogen, Cergy Pontoise, France) and transformed according to the manufacturer's instructions. After 120 hours of induction in 0.5% methanol, the secreted bppGalNAc-T1 was purified on Ni-NTA-agarose (Qiagen, Hilden, Germany) as described (Duclos et al. 2004). Fractions containing enzymatic activity were pooled and dialyzed against ultra-pure water, the protein was freeze-dried and stored at −20° C. until use. The specific activity of the recombinant bppGalNAc-T1 was tested as previously described (Duclos et al. 2004) and estimated to 3 U/mg protein (1 unit transfers 1 µmole of GalNAc per min at 37° C. to the acceptor peptide [STP]5).

In Vitro GalNAc Transfer to MUC6 Proteins

1. Using MCF7 Extracts

Optimal conditions for in vitro glycosylation of both MUC6 proteins were selected after testing different conditions assays in an analytical scale and characterizing the resulting glycoproteins by SELDI-TOF MS (Ciphergen Biosystems, California) as described in example 2. Briefly, a microsome extract of MCF7 breast cancer cells was incubated at 37° C. with UDP-GalNAc and purified MUC6-1 or MUC6-2 in 50 mM imidazole pH 7.2 containing 15 mM MnCl2 and 0.1% Triton-X100. Aliquots were taken at different times and frozen at −20° C. IMAC30 chip array surfaces were activated with 100 mM NiCl2 at room temperature for 15 minutes and then washed with water and PBS. Spots were incubated with the crude glycosylation mix aliquots for 40 minutes at room temperature using the bio-processor adaptor, and then washed with 0.1% Triton-X100 in PBS (2×5 min), PBS (3×2 min) and 5 mM HEPES (2×5 min). Chips were then read in the instrument (Ciphergen ProteinChip Reader, PBS II), and each array spot was laser-sampled. Spectra were treated using the Ciphergen ProteinChip software 3.2.1.

As a result, the following conditions were chosen and used for semi-preparative scale glycosylation transfer assays. Purified MUC6-1 or MUC6-2 (40-80 µM) was incubated with MCF7 extract (6 µg protein/µg mucin) and UDP-GalNAc (2 equivalents per Thr/Ser equivalent in mucin glycoproteins) in 50 mM imidazole pH 7.2 containing 50 mM MnCl2 and 0.1% Triton-X100 at 37° C. After 24 hour-incubation, the same amounts of MCF7 extract and UDP-GalNAc were added and incubated for another 24 h. The resulting MUC6-1:Tn or MUC6-2:Tn were purified using Ni-NTA-agarose (Qiagen, Hilden, Germany) and then subjected to reversed phase HPLC using a Perkin-Elmer pump system with an UV detector at 230 nm. The column was a Symmetry 300™ C18 (5 µm, 300 Å, 3.9×250 mm) (Waters, France). Elution was carried out with a linear gradient of 10-60% acetonitrile in 0.1% trifluoracetic acid in water at a flow rate of 1 mL/min (over 30 min). The peak was collected and then lyophilized. The MUC6-1:Tn and MUC6-2:Tn glycoproteins were characterized by AAA and mass spectrometry.

2. Using bppGalNAc-T1

Optimal semi-preparative optimal conditions of GalNAc transfer using bppGalNAc-T1 were set up using the Ciphergen® technology as described for the MCF7 extracts. MUC6-1 or MUC6-2 purified protein (40-80 µM) was incubated with UDP-GalNAc (2 equivalents per Thr/Ser equivalent in mucin glycoproteins) and bppGalNAc-T1 (0.1 µg/µg mucin) in 50 mM MES, pH 6.5 containing 15 mM MnCl2 for 24 h at 37° C. The resulting MUC6-1:Tn or MUC6-2:Tn was directly subjected to reverse phase HPLC and purified as explained above. The peak was collected, lyophilized and characterized by AAA and mass spectrometry.

Antibodies

The mAb 83D4 (IgM) (Pancino et al. 1991), which recognizes specifically the Tn antigen (Osinaga et al. 2000), was produced from a mouse immunized with cell suspensions obtained from formalin-fixed paraffin-embedded sections of an invasive human breast cancer (Pancino et al. 1990). It was then precipitated from ascitic fluids by dialysis against demineralized water at 4° C., dissolved in a small volume of 0.5 M NaCl in PBS, and purified by gel-filtration chromatography on Sephacryl™ S-200.

The anti-Tn mAb MLS128 (IgG1) (MLS128 mAb (p50): Numata et al. 1990), was obtained from a mouse immunized with human colonic cancer cells (LS180) (Numata et al., 1990) and purified by affinity chromatography on protein A-Sepharose®. Both anti-Tn mAbs recognize Tn residues organized in clusters (Nakada et al. 1993, Osinaga et al., 2000).

A MUC6-2 anti-serum was obtained by injection of BALB/c mice with 10 µg of purified MUC6-2 (see below) in alum (1 mg) and CpG (10 µg). Mice were injected i.p. at days 0, 21 and 42 and bleeded at days 20, 28 and 49. MUC6-2 anti-serum reactivity against MUC6-1 and MUC6-2 was confirmed by ELISA assays and the serum was stored at −20° C. until use.

Recognition of MUC6-1:Tn and MUC6-2:Tn by Anti-Tn mAbs and Anti-MUC6 Serum

Microtiter plates (Nunc, Denmark) were coated with the in vitro synthesized glycoproteins (0.1 µg/ml) and dried overnight. Plates were washed three times with 0.1% Tween 20 in PBS (PBS/T) and non-specific binding sites were blocked with 1% gelatin in PBS (PBS/G) for 2 h at 37° C. After washing, anti-Tn mAbs (83D4 or MLS128) or a polyclonal anti-MUC6 serum were added and incubated for 2 h at 37° C. After three washes with PBS/T, plates were incubated with goat anti-mouse IgM or anti-IgG peroxidase conjugates (Sigma, St. Louis, Mo.) diluted in PBS/TG for 1 h at 37° C. The plates were revealed using o-phenylenediamine/H2O2 and read photometrically at 492 nm in an ELISA auto-reader (Dynatech, Marnes la Coquette, France).

Western Blot Analysis of MUC6-Tn Glycoconjugates

MUC6-Tn glycoproteins were analyzed by Western blotting using an anti-His mAb (Qiagen, Hilden, Germany) and the anti-Tn mAb 83D4. (Glyco)conjugates were separated in a 13% SDS-polyacrylamide gel electrophoresis and transferred to nitrocellulose sheets (Amersham, Saclay, France) at 30 Volts overnight 20 mM Tris-HCl, pH 8.3, 192 mM glycine, 10% ethanol as already described (Towbin et al. 1992). Residual protein-binding sites were blocked by incubation with 3% bovine serum albumin (BSA) in PBS at 37° C. for 2 h. The nitrocellulose was then incubated either with the anti-His mAb or the anti-Tn mAb 83D4 for 2 h at 37° C. After three washes with PBS containing 0.1% Tween 20 and 1% BSA, the membrane was incubated for 1 h at room temperature with goat anti-mouse immunoglobulins conjugated to peroxidase (Sigma, St. Louis, Mo.) diluted in PBS containing 0.1% Tween-20 and 1.5% BSA, and reactions were developed with enhanced chemiluminiscence (ECL) (Amersham, Saclay, France). The same procedure was performed omitting the antibodies as a negative control.

Endotoxin Level Determination

The endotoxin level was determined in all glycosylated and non-glycosylated MUC6 proteins according the instructions of the manufacturer using the Limulus Amebocyte Lysate QCL-1000™ kit (Cambrex, France).

Immunization of Mice

Six- to eight-week old female BALB/c mice were purchased from Janvier (Le Genest Saint-Isle, France). Mice were injected i.p. three times with MUC6-2 or with MUC6-2:Tn(MCF7) (10 µg) mixed with alum (1 mg) (Serva, Heidelberg, Germany) plus CpG (10 µg) (Proligo, France) at three-week intervals (5 mice per group). Control mice received alum plus CpG alone. Sera were collected after each immunization and tested for the presence of anti-MUC6 and anti-Tn antibodies by ELISA and FACS.

Flow Cytometry

Mouse sera were tested at 1:500 dilution by flow cytometry on the human tumour cell line Jurkat (ATCC TIB-152). Cells were first incubated for 15 min with sera at 4° C. in PBS containing 5% fetal bovine serum and 0.1% sodium azide. Then, they were incubated 15 min with an anti-mouse IgG goat antibody conjugated to PE (Caltag, Burlingame, Calif.). Paraformaldehyde-fixed cells were analyzed on a FACScan™ flow cytometer (Becton Dickinson, San Jose, Calif.) and analyses were performed with CellQuest™ software (Becton Dickinson). For inhibition assays, cells were incubated with sera first mixed with serial dilutions of asialo-OSM [ovine submaxillary mucin] or deglycosylated-OSM prepared as previously described in Tettamanti G, Pigman W. (1968), Mendicino J, Sangadala S. (1998), Freire T, Casaravilla C, Carmona C, Osinaga E. (2003), for 15 min at 4° C. Then, the binding of antibodies to cells was revealed using an anti-mouse IgG goat antibody conjugated to PE. The anti-Tn mAb 83D4 was used as a positive control. An anti-CD4 mAb (Caltag, Burlingame, Calif.) was also used to verify that the binding of this mAb to the cells was not affected by the OSM proteins.

Example 2

Efficient Monitoring of Enzymatic Conjugation Reaction by Surface-Enhanced Laser Desorption/Ionization Time of Flight Mass Spectrometry (SELDI-TOF MS) for Process Optimization Abstract Efficient analysis of bioconjugation reactions is one the most challenging task for optimizing and eventually achieving the reproducible production of large amount of conjugates. In particular, the complexity of some reaction mixtures precludes the use of most of the existing methods, because of the presence of large amounts of contaminants. As an alternative method, we used surface-enhanced laser desorption/ionization time of flight mass spectrometry (SELDI-TOF MS) for monitoring an in vitro enzymatic transglycosylation of N-acetylgalactosamine residues to a recombinant mucin protein MUC6. For this reaction, catalyzed by the Uridine 5'-diphospho-N-acetylgalactosamine: polypeptide N-acetylgalactosaminyltransferases (ppGalNAcT), we used either a recombinant ppGalNAcT1, or a mixture of ppGalNAcTs contained in the MCF-7 tumour cell extracts.

In the present example, we show that SELDI-TOF MS offers unique advantages over the traditional methodologies. It is a rapid, accurate, sensitive, reproducible and very convenient analytical method for monitoring the course of a bioconjugation, even in heterogeneous samples such as cell extracts. SELDI-TOF MS proved very useful for optimizing the reaction parameters of the transglycosylation and for achieving the large scale preparation of Tn antigen-glycosylated mucins for anti-tumour immunotherapy applications.

Introduction

Bioconjugation technology has been widely used in nearly every discipline of the life sciences research (Niemeyer et al., 2004, Hermanson 1996). One of the application areas is the preparation of hapten-carrier conjugates for immunization purposes, antibody production and vaccine research. Indeed, small hapten molecules such as carbohydrates cannot elicit an efficient immune response on their own. To make them immunogenic, they must be coupled to a suitable carrier molecule, typically a protein.

The characteristics of the resulting conjugate play a critical role in the intensity and the quality of the immune response. In particular, several groups have reported the influence of the hapten density on the level, the specificity and the affinity of the produced antibodies (Hubbard et al. 1993, Singh et al., 2004). Careful follow-up of the conjugation is therefore very important to achieve the reproducible production of conjugates.

Different approaches are commonly employed to analyze these conjugates and to ascertain their optimal preparation. The choice of the method depends on the physico-chemical properties of both hapten and carrier, as well as on the cross-linking strategy. The most frequently used procedures involve mass spectrometry, associated with High Performance Liquid Chromatography (HPLC) or not (Oda et al. 2004, Singh et al. 2004, Weller et al., 2003, Weller et al. 2003, Adamczyk et al., 1996-9), gel filtration (Hermanson et al., 1993), absorption (Pauillac et al., 2002) and fluorescence (Singh et al. 2004, Weller et al. 2003) spectroscopy, gel electrophoresis (Pawlowski et al. 2000, Singh et al., 2004, Adamczyk et al. 1996), colorimetric assay for reactions involving sulfhydryl groups (Riddles et al. 1979), amino groups (Sashidhar et al. 1994), or carbohydrate residues (Manzi et al., 1993).

Although efficient, these existing methods suffer from several drawbacks. First, they often require further treatment of the samples, they are time-consuming, and they are not easy to perform when multiple samples are to be analyzed. Moreover, they are usually not very accurate and only give a rough estimate of the conjugate's molecular mass and integrity. Finally, the complexity of some reaction mixtures (cell extracts, sera, tissue homogenates, etc) can affect the effectiveness of the analysis adversely, due to the presence of large amounts of other compounds (lipids, detergents, salts, other proteins, etc).

Therefore, there is a need for rapid and sensitive analytical methods for monitoring bioconjugation reactions, particularly with complex and heterogeneous samples. Additionally, such efficient methods are essential in development, for optimizing the process and scaling up the production of the conjugates, while ensuring a batch-to-batch consistency.

ProteinChip® array technology or surface-enhanced laser desorption/ionization time of flight mass spectrometry (SELDI-TOF MS) allows the analysis of complex protein mixtures by combining two powerful techniques, chromatography and mass spectrometry. After selective retention on a chip surface, the compounds of interest are subsequently analyzed by a laser desorption/ionization mass spectrometer. This technique has been successfully used in many fields, e.g., biomarker discovery, study of biomolecular interactions, protein profiling, analysis of post-translational modifications, etc (Tang et al. 2004, Issaq et al. 2002).

As compared to these applications, very few examples have been described so far showing the use of SELDI-TOF for the monitoring of a reaction (whether chemical or enzymatic) or for the analysis of the resulting product. Recently, the direct analysis of peptides or proteins after either enzymatic digestion (Caputo et al. 2003, Merchant et al. 2000) or limited acid hydrolysis (Lin at al. 2001) has been successfully performed on-chip, with the aim of identifying protein sequences. On-chip enzymatic reactions and subsequent characterization have also been performed in order to study post-translational modifications. Using this method, the degree of glycosylation of a recombinant antibody has been monitored with a deglycosylation procedure using PNGase F (Cleverley at al. 2003) and the phosphorylation state of a peptide or a protein has been evaluated after the action of a kinase (Cardone at al. 1998) or a phosphatase (Voderwülbecke et al. 2005). This last example included a time course study.

In another characterization study, Hubalek et al. have described the analysis of biotinylated tryptic peptides after digestion of biotinylated recombinant human monoamine oxidases, and subsequent purification on an affinity column. Similarly, a peptide enzymatically released from a synthetic peptide related to the proteinase-activated receptor 2 was identified by SELDI-TOF MS (Dulon at al. 2005). Interestingly, SELDI-TOF MS has also allowed to follow the course of the autoactivation process of a bacterial protein, directly from the culture supernatant (Boyle et al. 2001).

Finally, the utility of SELDI-TOF MS has been demonstrated for monitoring the attachment of bacterial oligosaccharides to a protein, by a conjugation method using the squaric acid diester chemistry (Chernyak et al. 2001, Saksena at al. 2003). However, the reaction was a chemical ligation in a simple mixture composed of the synthetic linker-derivatized oligosaccharide, the protein carrier and the buffer.

To our knowledge, SELDI-TOF MS has never been used for monitoring an in vitro enzymatic conjugation reaction in a complex mixture.

Among the hapten molecules, carbohydrates are of particular interest since they are part of bacterial determinants and they are also tumour-associated antigens (TAA). As a result, a large number of carbohydrate-protein conjugates have been developed as vaccines against infectious diseases and cancer (Lo-Man et al. 2004). Preparation of various conjugates displaying the Tn antigen ($\alpha$-D-GalNAc-Ser/Thr) (Lo-Man et al. 2004, Kuduk et al., 1998, Slovin et al. 2003) which is a carbohydrate TAA over-expressed in breast, lung, prostate and colon cancers (Springer 1984, Freire et al., 2003) have been described. The resulting glycopeptides (Lo-Man et al., 2004) or glycoproteins (Kuduk et al. 1998, Slovin et al. 2003) have been shown to be highly promising vaccine candidates for targeting cancers.

However, the preparation of such conjugates relies on multi-step tedious syntheses and/or time-consuming purifications. To circumvent these difficulties, we developed an enzymatic approach for producing a protein glycoconjugate with a high Tn density.

Tn-mucins are attractive targets for anti-tumour immunotherapy since carbohydrates have been shown to be an essential part of tumour-associated structures within the mucins (Grinstead et al. 2002). As the protein backbone, is we chose the MUC6 gastric mucin (Toribara et al. 1993) which has been described in different tumours, including lung (Hamamoto et al., 2005, Nishiumi et al., 2003) and breast (De Bolos at al. 1995, Pereira et al. 2001) carcinomas. This mucin is a natural substrate of the Uridine 5'-diphospho-N-acetylgalactosamine (UDP-GalNAc):polypeptide N-acetylgalactosaminyltransferases (ppGalNAcTs, EC 2.4.1.41) which are the enzymes responsible for the Tn antigen synthesis in vivo.

In order to achieve the large scale preparation of MUC6-Tn conjugates for anti-tumour immunotherapy, we performed the in vitro enzymatic Tn antigen transfer onto the mucin acceptor. We describe herein the monitoring of the conjugation by SELDI-TOF MS and we show that this method is very rapid and efficient for optimizing the reaction parameters, including in complex mixtures.

Experimental Procedures

MUC6 Cloning and Expression in *E. coli*

A cDNA clone containing one tandem repeat of MUC6 was isolated from total cDNA of MCF7 breast cancer cells by RT-PCR and cloned into pGem®-T (Promega, France). The PCR products were designed to encode a half tandem repeat (87 amino acids) that were amplified as described in example 1.

The recombinants were expressed in *E. coli* Bli5 by induction with 1 mM IPTG and purified over Ni2+-nitriloacetic acid columns under denaturing conditions according to the manufacturer's (Qiagen, Germany) instructions.

Breast Cancer Cell Lines Extracts

Breast cancer cell line MCF-7 (ATCC number HTB-22) was grown to 90% confluence in Dulbecco's modified Eagle's medium (Life Technologies, Inc.) with 10% foetal bovine serum, 1 mM pyruvate and 2 mM glutamine and 5% $CO_2$ at 37° C. After trypsinization, cells were washed three times with phosphate-buffered saline (PBS), resuspended in PBS and homogenized. Cells were centrifuged at 3,000 g for 10 min at 4° C. and at 100,000 g for 1 h at 4° C. The resulting pellet was re-suspended in 0.1 M imidazole pH 7.2 and is 0.1% Triton™ X-100. Cell extracts were aliquoted and stored at −80° C. Protein concentration was determined by the BCA method (Sigma Chemical Co., St Louis, Mo.).
Recombinant Bovine Polypeptide GalNAc Transferase A soluble form of the bovine ppGalNAc-T1 (Duclos et al. 2004) was expressed in the yeast *Pichia pastoris* KM71H strain (Invitrogen) and purified as described in example 1.
In Vitro GalNAc Transfer to MUC6 Proteins Microsome fractions of MCF7 breast cancer cells were incubated at 37° C. with UDP-GalNAc and purified recombinant MUC6 in 50 mM imidazole pH 7.2 containing 50 mM MnCl2 and 0.1% Triton-X100. When recombinant ppGalNAc-T1 was used, the MUC6 purified protein was incubated with UDP-GalNAc in 50 mM MES, pH 6.5 for 24 hs at 37° C.

Aliquots were taken at different times and frozen at −20° C. The different reaction conditions are detailed in Table 2 below.

Triton-X100 in PBS (2×5 min), PBS (3×2 min) and 5 mM HEPES (2×5 min). Chips were then read in the PBS II instrument, and each array spot was laser-sampled. Spectra were treated using the Ciphergen ProteinChip software 3.2.1.
Results and Discussion The recombinant MUC6 protein was subjected to the transglycosylation reaction from the carbohydrate activated donor UDP-GalNAc in the presence of the enzyme, either a recombinant ppGalNAcT1 (Duclos et al. 2004), or a mixture of ppGalNAcTs contained in the MCF-7 tumour cell extracts (FIG. 6). Small aliquots of the reaction have been withdrawn and directly analyzed by SELDI-TOF MS after immobilization on the ProteinChip surface through immobilized metal affinity capture (IMAC30).

As shown in FIGS. 7A-7G, the ppGalNAcT1 can catalyze very efficiently the in vitro transfer of GalNAc residues onto the MUC6 protein. The reaction progress is monitored by the shift to higher masses, caused by the transfer of GalNAc

TABLE 2

Conditions of the tranglycosylation reaction, and average GalNAc amount of the resulting conjugates

| Fig. | UDP-GalNAc amount (eq)$^a$ | Enzyme amount (μg of protein/10 μg mucine) | Reaction time(h) | Observed average molecular mass (Da)$^c$ | Change in mass (ΔM) | Average GalNAc amount/mucin (μM/M$_g$)$^d$ |
|---|---|---|---|---|---|---|
| 7A | 0 | 1 (ppGalNAcT1) | 24 | 12144.3 | — | — |
| 7B | 2 | 0.01 (ppGalNAcT1) | 24 | 13170.0 | 1025.7 | 5 (5.05) |
| 7C | 2 | 0.04 (ppGalNAcT1) | 24 | 13778.8 | 1634.5 | 8 (8.04) |
| 7D | 2 | 0.2 (ppGalNAcT1) | 24 | 15018.2 | 2873.9 | 14 (14.14) |
| 7E | 2 | 1 (ppGalNAcT1) | 24 | 16036.1 | 3891.8 | 19 (19.15) |
| 7F | 1 | 1 (ppGalNAcT1) | 24 | 15806.6 | 3662.3 | 18 (18.02) |
| 7G | 0.5 | 1 (ppGalNAcT1) | 24 | 15598.8 | 3454.5 | 17 (17.0) |
| 8A | 0 | 65 (MCF-7 cell extracts) | 24 | 12144.8 | — | — |
| 8B | 2 | 130 (MCF-7 cell extracts)$^b$ | 48 | 17037.3 | 4892.5 | 24 (24.08) |

In the above table 2:
$^a$The molar equivalent amount is expressed as compared to potential O-glycosylation sites (47 serine and threonine residues);
$^b$65 μg were added at the beginning of the reaction and addition of 65 μg was repeated at 24 hrs;
$^c$The average molecular mass of the neoglycoconjugate was calculated from the medium peak which is marked with an arrow on FIGS. 1 and 2;
$^d$Mass of GalNAc M$_g$ = 203.19.

The resulting MUC6-Tn was purified using Ni-NTA-agarose (Qiagen, Hilden, Germany) and then subjected to reversed phase HPLC using a Perkin-Elmer pump system with an UV detector at 230 nm. The column was a Symmetry 300™ C18 (5 μm, 300 Å, 3.9×250 mm) (Waters, France). Elution was carried out with a linear gradient of 10-60% acetonitrile in 0.1% trifluoracetic acid in water at a flow rate of 1 ml/min (over 30 min). The peak was collected and then lyophilized. The MUC6-Tn glycoprotein was characterized by amino acid analysis and mass spectrometry.
Reaction Monitoring by SELDI-TOF IMAC30 chip array surfaces were activated with 100 mM NiCl2 at room temperature for 15 minutes and then washed with water and PBS. Spots were incubated with total glycosylation mix aliquots for 40 minutes at room temperature using the bio-processor adaptor, and then washed with 0.1% residues, as compared with the mass of the starting material (FIG. 7A). The spectra display a set of peaks showing the incremental molecular masses of the conjugates and allowing to determine the average hapten-protein stoichiometry, as well as the distribution/polydispersity of the conjugates.

The transglycosylation reaction was studied under various experimental conditions (see Table 2).

The extent of transfer was analyzed with 2 eq of UDP-GalNAc donor (the molar equivalent amount refers to the potential O-glycosylation sites, i.e., the total serine and threonine residues) and variable amounts of the recombinant ppGalNAcT1, after 24 h incubation. As shown on FIG. 7B-7E, the addition of enzyme results in a pronounced and progressive spectra shift showing significant increase in glycosylation with an average Tn amount from 5 (FIG. 7B) to 19 (FIG. 7E).

Further addition of enzyme alone or enzyme together with UDP-GalNAc did not significantly improve the transfer. Likewise, longer incubation period than 24 h produced no observable increase in molecular mass, showing that a maximum Tn level has been reached, at least in these types of conditions.

The effect of the amount of donor is presented in Panels E-G (FIG. 7). When lower quantities of UDP-GalNAc were used, the SELDI-TOF MS profile was found to be comparable, although a slight decrease in transfer is observed with 0.5 eq of donor (FIG. 7G).

In order to produce large amounts of conjugates while saving the expensive donor UDP-GalNAc, we chose the experimental conditions of FIG. 7F for scaling up the reaction (1 eq of UDP-GalNAc and 1 μg of enzyme/10 μg of MUC6). When the transglycosylation was performed on semi-preparative quantities (mg range of mucin), the number of transferred GalNAc residues was found to be virtually the same as the one obtained at the analytical level. As a result, the preparation of multi-milligrams of neoglycoconjugates has been achieved and the evaluation of their immunological properties is reported in example 1.

Enlargement of the representative spectrum with the selected conditions (FIG. 7F) shows the mass increment details (FIG. 8A). The difference between each peak corresponds to the expected average mass of a single GalNAc residue (203.193), demonstrating that SELDI-TOF MS is a resolutive method, at least in this molecular mass range. In contrast, the reverse phase HPLC profile does not show any separation of the different species (FIG. 8B).

SELDI-TOF was then applied to the analysis of transglycosylation in more complex mixtures, that is with the ppGalNAcTs catalysts contained in extracts from MCF-7 tumour cells (FIG. 9). The mass distribution obtained with the crude mixture is similar to the one observed with the recombinant enzyme. However, the transfer rate is better since an average density of 24 Tn/protein molecule has been achieved after 50 h of reaction and two additions of cell extracts (FIG. 9B). The fact that the resulting maximum Tn-protein stoichiometry is higher than in the case of the ppGalNAcT T1 indicates that the transfer is not only limited by the protein conformation (lack of accessibility of serine and threonine residues) but also by the specificity of the enzymes. Interestingly, the presence of numerous contaminants in the cell extracts hardly affects the signal-to-noise ratio, showing that SELDI-TOF can be useful for such complex analysis.

Therefore, although the monitoring of a chemical conjugation reaction has been reported previously by P. Kováč and co-workers (Chernyak et al. 2001, Saksena et al. 2003), we show here that such monitoring can also be done for an enzymatic reaction in a complex mixture (cell extracts) without any interference from contaminants. These results imply that SELDI-TOF MS is a powerful tool for monitoring a bioconjugation reaction. This technique provides a very efficient alternative to the traditional analysis methods.

First, it is a sensitive and accurate method since the conjugates could be efficiently analyzed from as few as 10 ng (1 pmol range), at least in the molecular mass range of 10,000-20,000 with mass increments of approximately 203. The traditional protein carriers which are used for immunization purposes have usually higher molecular mass, from approximately 60,000 (Bovine Serum Albumin or BSA, diphtheria toxoid) to several millions (Keyhole Limpet Hemocyanin or KLH). The accuracy and resolution of SELDI-TOF MS will be definitely limited in the higher molecular mass range, in particular for the KLH. This will also depend on the molecular mass of the hapten. In order to overcome these problems, the use of ZipTip® pipette tips can be considered. This method involves a microscale clean-up of the sample which then can be applied to high performance mass spectrometers (MALDI or electrospray) allowing efficient analyses in the high molecular weight range. However it is noteworthy that, for low molecular weights, ProteinChip® array technology remains simpler since it allows the purification step and the mass analysis on the same device. This eliminates the need for a transfer step and results in an optimal recovery of the sample.

Second, the method is very rapid, since it can be performed directly on the crude reaction without the need to purify or to derivatize the sample prior to analysis. In addition, the fact that several samples can be easily analyzed in parallel can be very valuable for studying the impact of various conditions on the efficiency of the conjugation. SELDI-TOF MS is therefore is potentially very useful for high-throughput optimization strategies.

Finally, our findings indicate that SELDI-TOF MS is suitable for analyzing complex crude samples from in vitro enzymatic conjugations.

It may also be directly applicable to monitor intracellular reactions performed in vivo. Such analyses have already been reported on crude fermentation or cell culture sources in order to optimize recombinant protein production (Clerverley et al. 2003, Savage et al. 2004) or to analyze the secretion and autoactivation of a bacterial protein (Boyle et al. 2001). Similar studies on mucin proteins are currently underway in the laboratory.

ABBREVIATIONS

BCA: bicinchoninic acid; BSA: bovine serum albumin; HEPES: 4-(2-hydroxyethyl)-piperazine-1-ethane sulfonic acid; HPLC: High Performance Liquid Chromatography; IPTG: isopropyl-β-D-thiogalactoside; mAb: monoclonal antibody; MES: 2-(N-morpholino)ethanesulfonic acid; PBS: phosphate-buffered saline; PCR: polymerase chain reaction; ppGalNAc-T: UDP-N-acetylgalactosamine: polypeptide N-acetylgalactosaminyltransferase; SDS-PAGE: sodium dodecyl sulphate polyacrylamide gel electrophoresis; SELDI-TOF MS: Surface-enhanced laser desorption/ionization time-of-flight mass spectrometry; UDP-GalNAc: uridine 5'-diphospho-N-acetylgalactosamine

BIBLIOGRAPHIC REFERENCES

Abdel-Motal, U. M., Berg, L., Rosen, A., Bengtsson, M., Thorpe, C. J., Kihlberg, J., Dahmen, J., Magnusson, G., Karlsson, K. A., and Jondal, M. (1996) *Eur J Immunol* 26, 544-551.

Adamczyk, M.; Gebler, J. C.; Mattingly, P. G. (1996) Characterization of protein-hapten conjugates. 2. Electrospray mass spectrometry of bovine serum albumin-hapten conjugates. *Bioconjug. Chem.* 7, 475-481.

Agrawal, B., Gendler, S. J. and Longenecker, B. M. (1998) The biological role of mucins in cellular interactions and immune regulation: prospects for cancer immunotherapy. *Mol Med Today*, 4, 397-403.

Ajisaka, K. and Miyasato, M. (2000) Efficient synthesis of a sialyl T-antigen-linked glycopeptide by the chemoenzymatic method. *Biosci Biotechnol Biochem*, 64, 1743-1746.

Amigorena, S, and Bonnerot, C. (1999) Fc receptor signaling and trafficking: a connection for antigen processing. *Immunol Rev*, 172, 279-284.

Apostolopoulos, V., McKenzie, I. F. C. and Pietersz, G. A. (1996) Breast cancer immunotherapy: Current status and future prospects. *Immunol Cell Biol*, 74, 457-464.

Apostolopoulos, V., Yuriev, E., Ramsland, P. A., Halton, J., Osinski, C., Li, W., Plebanski, M., Paulsen, H., and McKenzie, I. F. (2003) *Proc Natl Acad Sci USA* 100, 15029-15034.

Bartman, A. E., Sanderson, S. J., Ewing, S. L., Niehans, G. A., Wiehr, C. L., Evans, M. K. and Ho, S. B. (1999) Aberrant expression of MUC5AC and MUC6 gastric mucin genes in colorectal polyps. *Int J Cancer*, 80, 210-218.

Bay, S., Lo-Man, R., Osinaga, E., Nakada, H., Leclerc, C. and Cantacuzene, D. (1997) Preparation of a multiple antigen glycopeptide (MAG) carrying the Tn antigen. A possible approach to a synthetic carbohydrate vaccine. *J Peptide Res*, 49, 620-625.

Boyle, M. D.; Romer, T. G.; Meeker, A. K.; Sledjeski, D. D. (2001) Use of surface-enhanced laser desorption ionization protein chip system to analyze streptococcal exotoxin B activity secreted by *Streptococcus pyogenes. J. Microbiol. Methods* 46, 87-97.

Caputo, E.; Moharram, R.; Martin, B. M. (2003) Methods for on-chip protein analysis. *Anal. Biochem.* 321, 116-124.

Cardone, M. H.; Roy, N.; Stennicke, H. R.; Salvesen, G. S.; Franke, T. F.; Stanbridge, E.; Frisch, S.; Reed, J. C. (1998) Regulation of cell death protease caspase-9 by phosphorylation. *Science* 282, 1318-1321.

Chen, Y., Zhao, Y. H., Kalaslavadi, T. B., Hamati, E., Nehrke, K., Le, A. D., Ann, D. K. and Wu, R. (2004) Genome-wide search and identification of a novel gel-forming mucin MUC19/Muc19 in glandular tissues. *Am J Respir Cell Mol Biol*, 30, 155-165.

Cheng, L., Tachibana, K., Iwasaki, H., Kameyama, A., Zhang, Y., Kubota, T., Hiruma, T., Kudo, T., Guo, J. M. and Narimatsu, H. (2004) Characterization of a novel human UDP-GalNAc transferase, pp-GalNAc-T15. *FEBS Lett*, 566, 17-24.

Chernyak, A.; Karavanov, A.; Ogawa, Y.; Kovac, P. (2001) Conjugating oligosaccharides to proteins by squaric acid diester chemistry: rapid monitoring of the progress of conjugation, and recovery of the unused ligand. *Carbohydr. Res.* 330, 479-486.

Cleverley, S.; Bengio, S.; Boschetti, E.; Spencer, J. (2003) Direct "on-chip" protein-expression monitoring. *Genet. Eng. News* 23, Cool, D. R.; Hardiman, A. (2004) C-terminal sequencing of peptide hormones using carboxypeptidase Y and SELDI-TOF mass spectrometry. *Biotechniques* 36, 32-34.

Danishefsky, S. J.; Allen, J. R. (2000) From the laboratory to the clinic: a retrospective on fully synthetic carbohydrate-based anticancer vaccines. *Angew. Chem. Int. Ed.* 39, 836-863.

De Bolos, C., Garrido, M. and Real, F. X. (1995) MUC6 apomucin shows a distinct normal tissue distribution that correlates with Lewis antigen expression in the human stomach. *Gastroenterology*, 109, 723-734.

Duclos, S., Da Silva, P., Vovelle, F., Piller, F. and Piller, V. (2004) Characterization of the UDP-N-acetylgalactosamine binding domain of bovine polypeptide alphaN-acetylgalactosaminyltransferase T1. *Protein Eng Des Sel*, 17, 635-646.

Dulon, S.; Leduc, D.; Cottrell, G. S.; D'Alayer, J.; Hansen, K. K.; Bunnett, N. W.; Hollenberg, M. D.; Pidard, D.; Chignard, M. (2005) *Pseudomonas aeruginosa* elastase disables PAR2 in repiratory epithelial cells. *Am. J. Respir. Cell Mol. Biol. in press,*

Filshie, R. J., Zannettino, A. C., Makrynikola, V., Gronthos, S., Henniker, A. J., Bendall, L. J., Gottlieb, D. J., Simmons, P. J. and Bradstock, K. F. (1998) MUC18, a member of the immunoglobulin superfamily, is expressed on bone marrow fibroblasts and a subset of hematological malignancies. *Leukemia*, 12, 414-421.

Finn, O. J., Jerome, K. R., Henderson, R. A., Pecher, G., Domenech, N., Magarian-Blander, J. and Barratt-Boyes, S. M. (1995) MUC-1 epithelial tumour mucin-based immunity and cancer vaccines. *Immunol Rev*, 145, 61-89.

Freire, T., Bay, B., von Mensdorff-Pouilly, S, and Osinaga, E. (2005) Molecular basis of incomplete O-gycan synthesis in MCF-7 breast cancer cells: putative role of MUC6 in Tn antigen expression. *Cancer Res*, 65, 7880-7887.

Freire, T.; Osinaga, E. (2003) Immunological and biomedical relevance of the Tn antigen. *Immunology (Spain)* 22, 27-38.

Freire T, Casaravilla C, Carmona C, Osinaga E. (2003) *Int J. Parasitol.* 33, 47-56.

Gendler, S. J. and Spicer, A. P. (1995) Epithelial Mucin Genes. *Annu Rev Physiol*, 57, 607-634.

George, S. K., Schwientek, T., Holm, B., Reis, C. A., Clausen, H. and Kihlberg, J. (2001) Chemoenzymatic synthesis of sialylated glycopeptides derived from mucins and T-cell stimulating peptides. *J Am Chem Soc*, 123, 11117-11125.

Gilewski, T., Adluri, S., Ragupathi, G., Zhang, S., Yao, T. J., Panageas, K., Moynahan, M., Houghton, A., Norton, L. and Livingston, P. O. (2000) Vaccination of high-risk breast cancer patients with mucin-1 (MUC1) keyhole limpet hemocyanin conjugate plus QS-21. *Clin Cancer Res*, 6, 1693-1701.

Glithero, A., Tormo, J., Haurum, J. S., Arsequell, G., Valencia, G., Edwards, J., Springer, S., Townsend, A., Pao, Y. L., Wormald, M., Dwek, R. A., Jones, E. Y., and Elliot, T. (1999) *Immunity* 10, 63-74.

Grinstead, J. S.; Koganty, R. R.; Krantz, M. J.; Longenecker, B. M.; Campbell, A. P. (2002) Effect of glycosylation on MUC1 humoral immune recognition: is NMR studies of MUC1 glycopeptide-antibody interactions. *Biochemistry* 41, 9946-9961.

Grinstead, J. S., Schuman, J. T. and Campbell, A. P. (2003) Epitope mapping of antigenic MUC1 peptides to breast cancer antibody fragment B27.29: a heteronuclear NMR study. *Biochemistry*, 42, 14293-14305.

Guillem, P., Billeret, V., Buisine, M. P., Flejou, J. F., Lecomte-Houcke, M., Degand, P. R., Aubert, J. P., Triboulet, J. P. and Porchet, N. (2000) Mucin gene expression and cell differentiation in human normal, premalignant and malignant esophagus. *Int J Cancer*, 88, 856-861.

Gum, J. R., Jr., Crawley, S. C., Hicks, J. W., Szymkowski, D. E. and Kim, Y. S. (2002) MUC17, a novel membrane-tethered mucin. *Biochem Biophys Res Commun*, 291, 466-475.

Hamamoto, A., Abe, Y., Nishi, M., Fujimori, S., Ohnishi, Y., Yamazaki, H., Oida, Y., Miyazaki, N., Inada, K. I., Ueyama, Y., Iwasaki, M., Inoue, H. and Nakamura, M. (2005) Aberrant expression of the gastric mucin MUC6 in human pulmonary adenocarcinoma xenografts. *Int J Oncol*, 26, 891-896.

Haurum, J. S., Arsequell, G., Lellouch, A. C., Wong, S. Y., Dwek, R. A., McMichael, A. J., and Elliot, T. (1994) *J Exp Med* 180, 739-944.

Haurum, J. S., Hoier, I. B., Arsequell, G., Neisig, A., Valencia, G., Zeuthen, J., Neefjes, J., and Elliot, T. (1999) *J Exp Med* 190, 145-150.

Hermanson, G. T. (1996) Bioconjugate techniques. Academic Press.

Higuchi, T., Orita, T., Nakanishi, S., Katsuya, K., Watanabe, H., Yamasaki, Y., Waga, I., Nanayama, T., Yamamoto, Y., Munger, W., Sun, H. W., Falk, R. J., Jennette, J. C., Alcorta, D. A., Li, H., Yamamoto, T., Saito, Y. and Nakamura, M. (2004) Molecular cloning, genomic structure, and expression analysis of MUC20, a novel mucin protein, up-regulated in injured kidney. *J Biol Chem*, 279, 1968-1979.

Hilkens, J., Ligtenberg, M. J. L., Vos, H. L. and Litvinov, S. V. (1992) Cell Membrane-Associated Mucins And Their Adhesion-Modulating Property. *Trends Biochem Sci*, 17, 359-363.

Ho, S. B., Roberton, A. M., Shekels, L. L., Lyftogt, C. T., Niehans, G. A. and Toribara, N. W. (1995) Expression cloning of gastric mucin complementary DNA and localization of mucin gene expression. *Gastroenterology*, 109, 735-747.

Hollingsworth, M. A. and Swanson, B. J. (2004) Mucins in cancer: Protection and control of the cell surface. *Nat Rev Cancer*, 4, 45-60.

Houen, G.; Olsen, D. T.; Hansen, P. R.; Petersen, K. B.; Barkholt, V. (2003) Preparation of Bioconjugates by Solid-Phase Conjugation to Ion Exchange matrix-adsorbed carrier proteins. *Bioconjug. Chem.* 14, 75-79.

Hubbard, A. K.; Lohr, C. L.; Hastings, K.; Clarke, J. B.; Gandolfi, A. J. (1993) Immunogenicity studies of a synthetic antigen of alpha methyl dopa. *Immunopharmacol. Immunotoxicol.* 15, 621-637.

Irimura, T., Denda, K., Iida, S., Takeuchi, H. and Kato, K. (1999) Diverse glycosylation of MUC1 and MUC2: potential significance in tumour immunity. *J Biochem (Tokyo)*, 126, 975-985.

Issaq, H. J.; Veenstra, T. D.; Conrads, T. P.; Felschow, D. (2002) The SELDI-TOF MS approach to proteomics: protein profiling and biomarker identification. *Biochem. Biophys. Res. Commun.* 292, 587-592.

Kagan, E., Ragupathi, G., Yi, S. S., Reis, C. A., Gildersleeve, J., Kahne, D., Clausen, H., Danishefsky, S. J. and Livingston, P. O. (2005) Comparison of antigen constructs and carrier molecules for augmenting the immunogenicity of the monosaccharide epithelial cancer antigen Tn. *Cancer Immunol Immunother*, 54, 424-430.

Kato, K., Takeuchi, H., Miyahara, N., Kanoh, A., Hassan, H., Clausen, H. and Irimura, T. (2001) Distinct orders of GalNAc incorporation into a peptide with consecutive threonines. *Biochem Biophys Res Commun*, 287, 110-115.

Kuduk, S. D., Schwarz, J. B., Chen, X.-T., Glunz, P. W., Sames, D., Ragupathi, G., Livingston, P. O. and Danishefsky, S. J. (1998) Synthetic and immunological studies on clustered modes of mucin-related Tn and TF O-linked antigens: the preparation of a glycopeptide-based vaccine for clinical trials against prostate cancer. *J Am Chem Soc*, 120, 12474-12485.

Lin, S.; Tornatore, P.; King, D.; Orlando, R.; Weinberger, S. R. (2001) Limited acid hydrolysis as a means of fragmenting proteins isolated upon ProteinChip array surfaces. *Proteomics* 1, 1172-1184.

Lo-Man, R., Vichier-Guerre, S., Bay, S., Dériaud, E., Cantacuzene, D. and Leclerc, C. (2001) Anti-tumour immunity provided by a synthetic multiple antigenic glycopeptide displaying a tri-Tn glycotope. *J Immunol*, 166, 2849-2854.

Lo-Man, R., Vichier-Guerre, S., Perraut, R., Dériaud, E., Huteau, V., BenMohamed, L., Diop, O. M., Livingston, P. O., Bay, S, and Leclerc, C. (2004) A fully synthetic therapeutic vaccine candidate targeting carcinoma-associated Tn carbohydrate antigen induces specific antibodies in non-human primates. *Cancer Res*, 64, 4987-4994.

Longenecker, B. M., Willans, D. J., MacLean, G. D., Selvaraj, S., Suresh, M. R. and Noujaim, A. A. (1987) Monoclonal antibodies and synthetic tumour-associated glycoconjugates in the study of the expression of Thomsen-Friedenreich-like and Tn-like antigens on human cancers. *J Natl Cancer Inst*, 78, 489-496.

Mandel, U., Hassan, H., Therkildsen, M. H., Rygaard, J., Jakobsen, M. H., Juhl, B. R., Dabelsteen, E. and Clausen, H. (1999) Expression of polypeptide GalNAc-transferases in stratified epithelia and squamous cell carcinomas: immunohistological evaluation using monoclonal antibodies to three members of the GalNAc-transferase family. *Glycobiology*, 9, 43-52.

Manzi, A. E.; Varki, A. (1993) Glycobiology. *A Practical Approach*, Oxford University Press, New-York.

Marcaurelle, L. A. and Bertozzi, C. R. (2002) Recent advances in the chemical synthesis of mucin-like glycoproteins. *Glycobiology*, 12, 69R-77R.

Marcos, N. T., Cruz, A., Silva, F., Almeida, R., David, L., Mandel, U., Clausen, H., Von Mensdorff-Pouilly, S, and Reis, C. A. (2003) Polypeptide GalNAc-transferases, ST6GalNAc-transferase I, and ST3Gal-transferase I expression in gastric carcinoma cell lines. *J Histochem Cytochem*, 51, 761-771.

Mendicino J, Sangadala S. (1998) *Mol Cell Biochem.* 185, 135-45.

Merchant, M.; Weinberger, S. R. (2000) Recent advancements in surface-enhanced laser desorption/ionization-time of flight-mass spectrometry. *Electrophoresis* 21, 1164-1177.

Moniaux, N., Escande, F., Porchet, N., Aubert, J. P. and Batra, S. K. (2001) Structural organization and classification of the human mucin genes. *Front Biosci*, 6, D1192-D1206.

Nakada, H., Inoue, M., Numata, Y., Tanaka, N., Funakoshi, I., Fukui, S., Mellors, A. and Yamashina, I. (1993) Epitopic structure of Tn glycophorin A for an anti-Tn antibody (MLS 128). *Proc Natl Acad Sci USA*, 90, 2495-2499.

Niemeyer, C. M. (2004) Bioconjugation protocols: Strategies and methods. *Methods in Molecular Biology, Volume 283*, Humana Press, Totowa.

Nishiumi, N., Abe, Y., Inoue, Y., Hatanaka, H., Inada, K., Kijima, H., Yamazaki, H., Tatematsu, M., Ueyama, Y., Iwasaki, M., Inoue, H. and Nakamura, M. (2003) Use of 11p15 mucins as prognostic factors in small adenocarcinoma of the lung. *Clin Cancer Res*, 9, 5616-5619.

Nishiumi, N.; Abe, Y.; Inoue, Y.; Hatanaka, H.; Inada, K.; Kijima, H.; Yamazaki, H.; Tatematsu, M.; Ueyama, Y.; Iwasaki, M.; Inoue, H.; Nakamura, M. (2003) Use of 11p15 mucins as prognostic factors in small adenocarcinoma of the lung. *Clin. Cancer Res.* 9, 5616-5619.

Numata, Y., Nakada, H., Fukui, S., Kitagawa, H., Ozaki, K., Inoue, M., Kawasaki, T., Funakoshi, I. and Yamashina, I. (1990) A monoclonal antibody directed to Tn antigen. *Biochem Biophys Res Commun*, 170, 981-985.

Oda, M.; Sato-Nakamura, N.; Azuma, T. (2004) Molecular characterization of monovalent and multivalent hapten-protein conjugates for analysis of the antigen-antibody interaction. *Anal. Biochem.* 333, 365-371.

Osinaga, E., Bay, S., Tello, D., Babino, A., Pritsch, O., Assemat, K., Cantacuzene, D., Nakada, H. and Alzari, P. (2000) Analysis of the fine specificity of Tn-binding proteins using synthetic glycopeptide epitopes and a biosensor based on surface plasmon resonance spectroscopy. *FEBS Lett,* 469, 24-28.

Pallesen, L. T., Berglund, L., Rasmussen, L. K., Petersen, T. E. and Rasmussen, J. T. (2002) Isolation and characterization of MUC15, a novel cell membrane-associated mucin. *Eur J Biochem,* 269, 2755-2763.

Pancino, G. F., Osinaga, E., Vorauher, W., Kakouche, A., Mistro, D., Charpin, C. and Roseto, A. (1990) Production of a monoclonal antibody as immunohistochemical marker on paraffin embedded tissues using a new immunization method. *Hybridoma,* 9, 389-395.

Pancino G, Osinaga E, Charpin C, Mistro D, Barque J P, Roseto A. (1991) *Purification and characterisation of a breast-cancer-associated glycoprotein not expressed in normal breast and identified by monoclonal antibody 83D4.* Br J. Cancer. 63, 390-8

Pauillac, S.; Naar, J.; Mouratou, B.; Guesdon, J. L. (2002) Application of a modified version of Habeeb's trinitrophenylation method for the characterization of hapten-protein conjugates in a reversed micellar medium. *J. Immunol. Methods* 263, 75-83.

Pawlowski, A.; Kallenius, G.; Svenson, S. B. (2000) Preparation of pneumococcal capsular polysaccharide-protein conjugate vaccines utilizing new fragmentation and conjugation technologies. *Vaccine* 18, 1873-1885.

Pereira, M. B., Dias, A. J., Reis, C. A. and Schmitt, F. C. (2001) Immunohistochemical study of the expression of MUC5AC and MUC6 in breast carcinomas and adjacent breast tissues. *J Clin Pathol,* 54, 210-213.

Podolsky D. K. (1985) Oligosaccharide structures of isolated human colonic mucin species. *The Journal of Biological Chemistry,* 260(29): 15510-15515.

Reis, C. A., David, L., Carvalho, F., Mandel, U., de Bolos, C., Mirgorodskaya, E., Clausen, H. and Sobrinho-Simoes, M. (2000) Immunohistochemical study of the expression of MUC6 mucin and co-expression of other secreted mucins (MUC5AC and MUC2) in human gastric carcinomas. *J Histochem Cytochem,* 48, 377-388.

Riddles, P. W.; Blakeley, R. L.; Zerner, B. (1979) Ellman's reagent: 5,5'-dithiobis(2-nitrobenzoic acid)—a reexamination. *Anal. Biochem.* 94, 75-81.

Robbe C. et al. (2004) Structural diversity and specific distribution of O-glycans in normal human mucins along the intestinal tract. Biochemical Journal 384 (Pt 2): 307-316.

Rousseau, K., Byrne, C., Kim, Y. S., Gum, J. R., Swallow, D. M. and Toribara, N. W. (2004) The complete genomic organization of the human MUC6 and MUC2 mucin genes. *Genomics,* 83, 936-939.

Saksena, R.; Chernyak, A.; Karavanov, A.; Kovac, P. (2003) Conjugating low molecular mass carbohydrates to proteins. 1. Monitoring the progress of conjugation. *Methods Enzymol.* 362, 125-139.

Sashidhar, R. B.; Capoor, A. K.; Ramana, D. (1994) Quantitation of epsilon-amino group using amino acids as reference standards by trinitrobenzene sulfonic acid. A simple spectrophotometric method for the estimation of hapten to carrier protein ratio. *J. Immunol. Methods* 167, 121-127.

Savage, C. (2003) Ciphergen segments proteomics applications. *Genet. Eng. News* 23.

Segal-Eiras, A. and Croce, M. V. (1997) Breast cancer associated mucin: a review. *Allergol Immunopathol (Madr),* 25, 176-181.

Singh, K. V.; Kaur, J.; Varshney, G. C.; Raje, M.; Suri, C. R. (2004) Synthesis and characterization of hapten-protein conjugates for antibody production against small molecules. *Bioconjug. Chem.* 15, 168-173.

Singhal, A., Fohn, M. and Hakomori, S. (1991) Induction of alpha-N-acetylgalactosamine-O-serine/threonine (Tn) antigen-mediated cellular immune response for active immunotherapy in mice. *Cancer Res,* 51, 1406-1411.

Slovin, S. F., Ragupathi, G., Musselli, C., Olkiewicz, K., Verbel, D., Kuduk, S. D., Schwarz, J. B., Sames, D., Danishefsky, S., Livingston, P. O. and Scher, H. I. (2003) Fully synthetic carbohydrate-based vaccines in biochemically relapsed prostate cancer: clinical trial results with alpha-N-acetylgalactosamine-O-serine/threonine conjugate vaccine. *J Clin Oncol,* 21, 4292-4298.

Sorensen, A. L., Reis, C. A., Tarp, M. A., Mandel, U., Ramachandran, K., Sankaranarayanan, V., Schwientek, T., Graham, R., Taylor-Papadimitriou, J., Hollingsworth, M. A., Burchell, J. and Clausen, H. (2005) Chemoenzymatically synthesized multimeric Tn/STn MUC1 glycopeptides elicit cancer specific anti-MUC1 antibody responses and override tolerance. *Glycobiology.*

Speir, J. A., Abdel-Motal, U. M., Jondal, M., and Wilson, I. A. (1999) *Immunity* 10, 51-61.

Springer, G. F. (1984) T and Tn, general carcinoma autoantigens. *Science* 224, 1198-1206.

Springer, G. F. (1984) T and Tn, general carcinoma autoantigens. *Science,* 224, 1198-1206.

Springer, G. F. (1997) Immunoreactive T and Tn epitopes in cancer diagnosis, prognosis, and immunotherapy. *J Mol Med,* 75, 594-602.

Springer, G. F., Desai, P. R., Tegtmeyer, H., Spencer, B. D. and Scanlon, E. F. (1993) Pancarcinoma T/Tn antigen detects human carcinoma long before biopsy does and its vaccine prevents breast carcinoma recurrence. *Ann NY Acad Sci,* 690, 355-357.

Takeuchi, H., Kato, K., Hassan, H., Clausen, H. and Irimura, T. (2002) O-GalNAc incorporation into a cluster acceptor site of three consecutive threonines. Distinct specificity of GalNAc-transferase isoforms. *Eur J Biochem,* 269, 6173-6183.

Tang, N.; Tornatore, P.; Weinberger, S. R. (2004) Current developments in SELDI affinity technology. *Mass Spectrom. Rev.* 23, 34-44.

Ten Hagen, K. G., Fritz, T. A. and Tabak, L. A. (2003) All in the family: the UDP-GalNAc:polypeptideN-acetylgalactosaminyltransferases. *Glycobiology,* 13, 1R-16R.

Tettamanti G, Pigman W. (1968) *Arch Biochem Biophys.* 124, 41-50.

Toribara, N. W., Roberton, A. M., Ho, S. B., Kuo, W. L., Gum, E., Hicks, J. W., Gum, J. R., Jr., Byrd, J. C., Siddiki, B. and Kim, Y. S. (1993) Human gastric mucin. Identification of a unique species by expression cloning. *J Biol Chem,* 268, 5879-5885.

Towbin, H., Staehelin, T. and Gordon, J. (1992) Electrophoretic transfer of proteins from polyacrylamide gels to nitrocellulose sheets: procedure and some applications. 1979. *Biotechnology,* 24, 145-149.

Toyokuni, T., Hakomori, S, and Singhal, A. K. (1994) Synthetic carbohydrate vaccines: synthesis and immunogenicity of Tn antigen conjugates. *Bioorg Med Chem,* 2, 1119-1132.

Vinall, L. E., Hill, A. S., Pigny, P., Pratt, W. S., Toribara, N., Gum, J. R., Kim, Y. S., Porchet, N., Aubert, J. P. and Swallow, D. M. (1998) Variable number tandem repeat polymorphism of the mucin genes located in the complex on 11p15.5. *Hum Genet,* 102, 357-366.

von Mensdorff-Pouilly, S., Kinarsky, L., Engelmann, K., Baldus, S. E., Verheijen, R. H., Hollingsworth, M. A., Pisarev, V., Sherman, S. and Hanisch, F. G. (2005) Sequence-variant repeats of MUC1 show higher conformational flexibility, are less densely O-glycosylated and induce differential B lymphocyte responses. *Glycobiology,* 15, 735-746.

Vorderwülbecke, S.; Cleverley, S.; Weinberger, S. C.; Wiesner, A. (2005) Protein quantification by the SELDI-TOF-MS-based ProteinChip System® system. *Nature Methods* 2, 393-395.

Weller, M. G.; Diemer, M.; Wersching, C.; Niessner, R.; Sochor, H. (2003) Development of antibodies for the detection of N-acetyl-glufosinate. *J Agric Food Chem* 51, 6668-6675.

Williams, S. J., Wreschner, D. H., Tran, M., Eyre, H. J., Sutherland, G. R. and McGuckin, M. A. (2001) Muc13, a novel human cell surface mucin expressed by epithelial and hemopoietic cells. *J Biol Chem,* 276, 18327-18336.

Xu, Y., Gendler, S. J., and Franco, A. (2004) *J Exp Med* 199, 707-716.

Yin, B. W. and Lloyd, K. O. (2001) Molecular cloning of the CA125 ovarian cancer antigen: identification as a new mucin, MUC16. *J Biol Chem,* 276, 27371-27375.

The invention claimed is:

1. An immunogenic Tn-based mucin glycoconjugate, wherein the Tn-based mucin glycoconjugate is prepared by enzymatically adding GalNAc moieties to at least 40% of the Ser and Thr residues of an apomucin backbone in vitro to produce a glycoconjugate containing only O-linked GalNAc residues,
   wherein the apomucin backbone comprises SEQ ID NO:12, SEQ ID NO:9, SEQ ID NO:6, SEQ ID NO:7, or SEQ ID NO:15.

2. The immunogenic Tn-based mucin glycoconjugate of claim 1, wherein the apomucin backbone comprises SEQ ID NO:12.

3. The immunogenic Tn-based mucin glycoconjugate of claim 1, wherein the apomucin backbone comprises SEQ ID NO:9.

4. The immunogenic Tn-based mucin glycoconjugate of claim 1, wherein the apomucin backbone comprises SEQ ID NO:6.

5. The immunogenic Tn-based mucin glycoconjugate of claim 1, wherein the apomucin backbone comprises SEQ ID NO:7.

6. The immunogenic Tn-based mucin glycoconjugate of claim 1, wherein the apomucin backbone comprises SEQ ID NO:15.

7. A method for inducing an immune response comprising administering the immunogenic Tn-based mucin glycoconjugate of claim 1 to a human.

8. A method for inducing an immune response comprising administering the immunogenic Tn-based mucin glycoconjugate of claim 2 to a human.

9. A method for inducing an immune response comprising administering the immunogenic Tn-based mucin glycoconjugate of claim 3 to a human.

10. A method for inducing an immune response comprising administering the immunogenic Tn-based mucin glycoconjugate of claim 4 to a human.

11. A method for inducing an immune response comprising administering the immunogenic Tn-based mucin glycoconjugate of claim 5 to a human.

12. A method for inducing an immune response comprising administering the immunogenic Tn-based mucin glycoconjugate of claim 6 to a human.

* * * * *

```
                         SEQUENCE LISTING

<160> NUMBER OF SEQ ID NOS: 34

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic
      sense primer MUC6-F for one MUC6 tandem repeat

<400> SEQUENCE: 1
cgggatcctc cacctccttg gtgact                                              26

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      reverse primer MUC6-R for one MUC6 tandem repeat

<400> SEQUENCE: 2
ggaagctttt agaaaggtgg aacgtg                                              26

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      reverse primer MUC6-2R for 1/2 MUC6 tandem repeat

<400> SEQUENCE: 3
ggaagcttat taggatggtg tgtgga                                              26

<210> SEQ ID NO 4
<211> LENGTH: 203
<212> TYPE: PRT
<213> ORGANISM: Homo sapiens

<400> SEQUENCE: 4

Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Ser Thr Ser Leu Val Thr Pro Ser Thr His Thr Val Ile Thr
        35                  40                  45

Pro Thr His Ala Gln Met Ala Thr Ser Ala Ser Asn His Ser Ala Pro
    50                  55                  60
```

```
Thr Gly Thr Ile Pro Pro Pro Thr Thr Leu Lys Ala Thr Gly Ser Thr
 65                  70                  75                  80

His Thr Ala Pro Pro Ile Thr Pro Thr Thr Ser Gly Thr Ser Gln Ala
                 85                  90                  95

His Ser Ser Phe Ser Thr Asn Lys Thr Pro Thr Ser Leu His Ser His
            100                 105                 110

Thr Ser Ser Thr His His Pro Glu Val Thr Pro Thr Ser Thr Thr Thr
        115                 120                 125

Ile Thr Pro Asn Pro Thr Ser Thr Arg Thr Arg Thr Pro Val Ala His
    130                 135                 140

Thr Asn Ser Ala Thr Ser Ser Arg Pro Pro Pro Phe Thr Thr His
145                 150                 155                 160

Ser Pro Pro Thr Gly Ser Ser Pro Phe Ser Thr Gly Pro Met Thr
                165                 170                 175

Ala Thr Ser Phe Lys Thr Thr Thr Tyr Pro Thr Pro Ser Leu Pro
            180                 185                 190

Gln Thr Thr Pro Leu Thr His Val Pro Pro Phe
        195                 200
```

<210> SEQ ID NO 5
<211> LENGTH: 119
<212> TYPE: PRT
<213> ORGANISM: Homo sapiens

<400> SEQUENCE: 5

```
Met Gly Ser Ser His His His His His His Ser Ser Gly Leu Val Pro
 1               5                  10                  15

Arg Gly Ser His Met Ala Ser Met Thr Gly Gly Gln Gln Met Gly Arg
                 20                  25                  30

Gly Ser Ser Thr Ser Leu Val Thr Pro Ser Thr His Thr Val Ile Thr
            35                  40                  45

Pro Thr His Ala Gln Met Thr Thr Ser Ala Ser Ile His Ser Met Pro
        50                  55                  60

Thr Gly Thr Ile Pro Pro Pro Thr Thr Leu Met Ala Thr Gly Ser Thr
 65                  70                  75                  80

His Thr Ala Pro Leu Ile Thr Val Thr Thr Ser Arg Thr Ser Gln Val
                 85                  90                  95

His Ser Ser Phe Ser Thr Ala Lys Thr Ser Thr Ser Leu Leu Ser His
            100                 105                 110

Ala Ser Ser Thr His His Pro
        115
```

<210> SEQ ID NO 6
<211> LENGTH: 169
<212> TYPE: PRT
<213> ORGANISM: Homo sapiens

<400> SEQUENCE: 6

```
Ser Thr Ser Leu Val Thr Pro Ser Thr His Thr Val Ile Ala Pro Thr
 1               5                  10                  15

His Ala Gln Met Ala Thr Ser Ala Ser Ile His Ser Ala Pro Thr Gly
                 20                  25                  30

Thr Ile Pro Pro Pro Thr Thr Leu Lys Ala Thr Gly Ser Thr His Thr
            35                  40                  45

Ala Pro Pro Ile Thr Pro Thr Thr Ser Gly Thr Ser Gln Ala His Ser
        50                  55                  60
```

```
Ser Phe Ser Thr Asn Lys Thr Pro Thr Ser Leu His Ser His Thr Ser
 65                  70                  75                  80

Ser Thr His His Pro Glu Val Ala Pro Thr Ser Thr Thr Thr Ile Thr
                 85                  90                  95

Pro Asn Pro Thr Ser Thr Arg Thr Arg Thr Pro Val Ala His Thr Asn
            100                 105                 110

Ser Ala Thr Ser Ser Arg Pro Pro Pro Phe Thr Thr His Ser Pro
        115                 120                 125

Pro Thr Gly Ser Ser Pro Phe Ser Ser Thr Gly Pro Met Thr Ala Thr
            130                 135                 140

Ser Phe Lys Thr Thr Thr Thr Tyr Pro Thr Pro Ser Leu Pro Gln Thr
145                 150                 155                 160

Thr Pro Leu Thr His Val Pro Pro Phe
                165

<210> SEQ ID NO 7
<211> LENGTH: 169
<212> TYPE: PRT
<213> ORGANISM: Homo sapiens

<400> SEQUENCE: 7

Ser Thr Ser Leu Val Thr Ile Ser Thr His Thr Val Ile Thr Pro Thr
  1               5                  10                  15

His Pro Gln Met Ser Thr Ser Ala Tyr Ile His Ser Thr Pro Thr Gly
                 20                  25                  30

Thr Ile Ala Ser Pro Thr Thr Val Lys Ala Thr Arg Ser Thr Tyr Thr
             35                  40                  45

Ala Pro Leu Met Thr Ala Thr Thr Arg Ile Thr Ser Gln Ala His Ser
 50                  55                  60

Ser Ile Ser Thr Ala Lys Thr Ser Thr Ser Leu His Ser His Ala Ser
 65                  70                  75                  80

Ser Thr His His Pro Glu Val Thr Pro Thr Ser Thr Thr Asn Val Thr
                 85                  90                  95

Pro Lys Ser Thr Ser Arg Asp Thr Ser Thr Pro Val Thr His Thr Thr
            100                 105                 110

Ser Ala Thr Ser Ser Arg Pro Pro Thr Pro Ile Thr Thr His Ser Ser
        115                 120                 125

Pro Thr Arg Ser Ser Pro Leu Ser Ser Thr Gly Pro Met Thr Ala Thr
            130                 135                 140

Ser Ile Lys Thr Thr Thr Thr Tyr Pro Thr Pro Ser His Pro Gln Thr
145                 150                 155                 160

Thr Leu Thr Thr His Val Pro Pro Phe
                165

<210> SEQ ID NO 8
<211> LENGTH: 513
<212> TYPE: DNA
<213> ORGANISM: Homo sapiens

<400> SEQUENCE: 8
tccacctcct tggtgactcc aagtactcac acagtcatca cccctaccca cgcacagatg      60
gccacatctg cctccaacca ctcagcgcca acaggtacca ttcctccacc aacaacgctc     120
aaggccacag ggtccaccca cacagcccca ccaataacgc cgaccaccag tgggaccagc     180
caagcccaca gctcattcag cacaaacaaa cacctacct cgctacattc acacacttcc      240
tccacacacc atcctgaagt cacccccaact tctactacca cgattactcc caaccccact     300
```

```
agtacacgca ccagaacccc tgtggcccac accaactcag ccaccagcag cagcaggcca    360
ccaccaccct tcaccacaca ctccccacct acagggagca gtcccttctc ttccacaggt    420
cccatgacgg caacatcctt caagaccacc actacctatc aacccccatc actccctcag    480
accacacctc tcactcatgt tccaccttttc taa                                 513
```

<210> SEQ ID NO 9
<211> LENGTH: 169
<212> TYPE: PRT
<213> ORGANISM: Homo sapiens

<400> SEQUENCE: 9

```
Ser Thr Ser Leu Val Thr Pro Ser Thr His Thr Val Ile Thr Pro Thr
1               5                   10                  15

His Ala Gln Met Ala Thr Ser Ala Ser Asn His Ser Ala Pro Thr Gly
            20                  25                  30

Thr Ile Pro Pro Thr Thr Leu Lys Ala Thr Gly Ser Thr His Thr
        35                  40                  45

Ala Pro Pro Ile Thr Pro Thr Thr Ser Gly Thr Ser Gln Ala His Ser
    50                  55                  60

Ser Phe Ser Thr Asn Lys Thr Pro Thr Ser Leu His Ser His Thr Ser
65                  70                  75                  80

Ser Thr His His Pro Glu Val Thr Pro Thr Ser Thr Thr Thr Ile Thr
                85                  90                  95

Pro Asn Pro Thr Ser Thr Arg Thr Arg Thr Pro Val Ala His Thr Asn
                100                 105                 110

Ser Ala Thr Ser Ser Arg Pro Pro Pro Phe Thr Thr His Ser Pro
            115                 120                 125

Pro Thr Gly Ser Ser Pro Phe Ser Ser Thr Gly Pro Met Thr Ala Thr
        130                 135                 140

Ser Phe Lys Thr Thr Thr Thr Tyr Pro Pro Pro Ser Leu Pro Gln Thr
145                 150                 155                 160

Thr Pro Leu Thr His Val Pro Pro Phe
                165
```

<210> SEQ ID NO 10
<211> LENGTH: 615
<212> TYPE: DNA
<213> ORGANISM: Homo sapiens

<400> SEQUENCE: 10

```
atgggcagca gccatcatca tcatcatcac agcagcggcc tggtgccgcg cggcagccat    60
atggctagca tgactggtgg acagcaaatg ggtcgcggat cctccacctc cttggtgact    120
ccaagtactc acacagtcat caccccctacc cacgcacaga tggccacatc tgcctccaac    180
cactcagcgc caacaggtac cattcctcca ccaacaacgc tcaaggccac agggtccacc    240
cacacagccc caccaataac gccgaccacc agtgggacca gccaagccca cagtcattc    300 agcacaaaca aaacacctac ctcgctacat tcacacactt cctccacaca ccatcctgaa    360
gtcaccccaa cttctactac cacgattact cccaaacccca ctagtacacg caccagaacc    420
cctgtggccc acaccaactc agccaccagc agcagcaggc caccaccacc cttcaccaca    480
cactccccac ctacagggag cagtcccttc tcttccacag gtcccatgac ggcaacatcc    540
ttcaagacca ccactaccta tccaaccccca tcactccctc agaccacacc tctcactcat    600 gttccaccttt tctaa                                                      615
```

<210> SEQ ID NO 11
<211> LENGTH: 258
<212> TYPE: DNA
<213> ORGANISM: Homo sapiens

<400> SEQUENCE: 11

```
tccacctcct tggtgactcc aagtactcac acagtcatca cccctaccca cgcacagatg    60
accacttctg cctccatcca ctcaatgcca acaggcacca ttcctccacc gacaacgctc   120
atggccacag ggtccacaca cacagcccca ctaataacag tgaccaccag taggaccagc   180
caagtccaca gctccttcag cacagccaaa acctctacat ccctcctctc ccatgcttcc   240
tccacacacc atccttaa                                                 258
```

<210> SEQ ID NO 12
<211> LENGTH: 85
<212> TYPE: PRT
<213> ORGANISM: Homo sapiens

<400> SEQUENCE: 12

```
Ser Thr Ser Leu Val Thr Pro Ser Thr His Thr Val Ile Thr Pro Thr
1               5                   10                  15

His Ala Gln Met Thr Thr Ser Ala Ser Ile His Ser Met Pro Thr Gly
            20                  25                  30

Thr Ile Pro Pro Pro Thr Thr Leu Met Ala Thr Gly Ser Thr His Thr
        35                  40                  45

Ala Pro Leu Ile Thr Val Thr Thr Ser Arg Thr Ser Gln Val His Ser
    50                  55                  60

Ser Phe Ser Thr Ala Lys Thr Ser Thr Ser Leu Leu Ser His Ala Ser
65                  70                  75                  80

Ser Thr His His Pro
                85
```

<210> SEQ ID NO 13
<211> LENGTH: 360
<212> TYPE: DNA
<213> ORGANISM: Homo sapiens

<400> SEQUENCE: 13

```
atgggcagca gccatcatca tcatcatcac agcagcggcc tggtgccgcg cggcagccat    60
atggctagca tgactggtgg acagcaaatg ggtcgcggat cctccacctc cttggtgact   120
ccaagtactc acacagtcat caccctacc acgcacaga tgaccacttc tgcctccatc     180
cactcaatgc caacaggcac cattcctcca ccgacaacgc tcatggccac agggtccaca   240
cacacagccc cactaataac agtgaccacc agtaggacca gccaagtcca cagctccttc   300
agcacagcca aaacctctac atccctcctc tcccatgctt cctccacaca ccatccttaa   360
```

<210> SEQ ID NO 14
<211> LENGTH: 10
<212> TYPE: PRT
<213> ORGANISM: Homo sapiens

<400> SEQUENCE: 14

```
Gly Thr Thr Pro Pro Thr Thr Leu Lys
1               5                   10
```

<210> SEQ ID NO 15
<211> LENGTH: 167

<212> TYPE: PRT
<213> ORGANISM: Homo sapiens

<400> SEQUENCE: 15

Ser Thr Ser Ser Val Thr Pro Ser Thr His Thr Val Ile Thr Pro Thr
1               5                   10                  15

His Ala Gln Met Ser Thr Ser Ala Ser Ile His Ser Thr Pro Thr Gly
            20                  25                  30

Thr Val Pro Pro Leu Thr Thr Arg Met Pro Gly Ser Thr Arg Thr
        35                  40                  45

Gly Pro Pro Met Thr Gly Thr Ile Ile Gln Thr Ser Lys Ala His Asn
    50                  55                  60

Ser Phe Ser Thr Ala Lys Thr Ser Thr Ser Leu His Ser His Ala Ser
65                  70                  75                  80

Ser Thr His His Pro Glu Thr Thr Pro Thr Ser Thr Thr Asn Ile Thr
                85                  90                  95

Pro Lys Ser Thr Ser Ala Gly Thr Ser Thr Pro Val Ala His Thr Thr
            100                 105                 110

Leu Ala Thr Ser Ser Arg Leu Pro Thr Thr Phe Thr Thr Phe Ser Pro
            115                 120                 125

Pro Thr Gly Ser Ser His Val Ser Ser Thr Gly Pro Met Thr Ala Thr
            130                 135                 140

Ser Ser Gln Thr Thr Thr Thr His Pro Pro Ser His Pro Gln Thr
145                 150                 155                 160

Thr Pro Leu Thr His Val Pro
                165

<210> SEQ ID NO 16
<211> LENGTH: 9
<212> TYPE: PRT
<213> ORGANISM: Homo sapiens

<400> SEQUENCE: 16

Leu Val Thr Pro Ser Thr His Thr Val
1               5

<210> SEQ ID NO 17
<211> LENGTH: 9
<212> TYPE: PRT
<213> ORGANISM: Homo sapiens

<400> SEQUENCE: 17

Gly Thr Ile Pro Pro Thr Thr Leu
1               5

<210> SEQ ID NO 18
<211> LENGTH: 9
<212> TYPE: PRT
<213> ORGANISM: Homo sapiens

<400> SEQUENCE: 18

Thr Leu Lys Ala Thr Gly Ser Thr His
1               5

<210> SEQ ID NO 19
<211> LENGTH: 9
<212> TYPE: PRT
<213> ORGANISM: Homo sapiens

<400> SEQUENCE: 19

```
Thr Ile Pro Pro Pro Thr Thr Leu Lys
1               5

<210> SEQ ID NO 20
<211> LENGTH: 9
<212> TYPE: PRT
<213> ORGANISM: Homo sapiens

<400> SEQUENCE: 20

Glu Val Thr Pro Thr Ser Thr Thr Thr
1               5

<210> SEQ ID NO 21
<211> LENGTH: 9
<212> TYPE: PRT
<213> ORGANISM: Homo sapiens

<400> SEQUENCE: 21

Thr Pro Ser Thr His Thr Val Ile Thr
1               5

<210> SEQ ID NO 22
<211> LENGTH: 9
<212> TYPE: PRT
<213> ORGANISM: Homo sapiens

<400> SEQUENCE: 22

Ile Pro Pro Pro Thr Thr Leu Lys Ala
1               5

<210> SEQ ID NO 23
<211> LENGTH: 9
<212> TYPE: PRT
<213> ORGANISM: Homo sapiens

<400> SEQUENCE: 23

Gly Arg Gly Ser Ser Thr Ser Leu Val
1               5

<210> SEQ ID NO 24
<211> LENGTH: 20
<212> TYPE: PRT
<213> ORGANISM: Homo sapiens

<400> SEQUENCE: 24

Gly Ser Thr Ala Pro Pro Ala His Gly Val Thr Ser Ala Pro Asp Thr
1               5                   10                  15

Arg Pro Ala Pro
            20

<210> SEQ ID NO 25
<211> LENGTH: 20
<212> TYPE: PRT
<213> ORGANISM: Mus musculus

<400> SEQUENCE: 25

Asp Ser Thr Ser Ser Pro Val His Ser Gly Thr Ser Ser Pro Ala Thr
1               5                   10                  15

Ser Ala Pro Glu
            20

<210> SEQ ID NO 26
<211> LENGTH: 23
<212> TYPE: PRT
```

<213> ORGANISM: Homo sapiens

<400> SEQUENCE: 26

Pro Thr Thr Thr Pro Ile Thr Thr Thr Thr Val Thr Pro Thr Pro
1               5                   10                  15

Thr Pro Thr Gly Thr Gln Thr
            20

<210> SEQ ID NO 27
<211> LENGTH: 11
<212> TYPE: PRT
<213> ORGANISM: Rattus norvegicus

<400> SEQUENCE: 27

Pro Ser Thr Pro Ser Thr Pro Pro Pro Ser Thr
1               5                   10

<210> SEQ ID NO 28
<211> LENGTH: 17
<212> TYPE: PRT
<213> ORGANISM: Homo sapiens

<400> SEQUENCE: 28

His Ser Thr Pro Ser Phe Thr Ser Ser Ile Thr Thr Thr Glu Thr Thr
1               5                   10                  15

Ser

<210> SEQ ID NO 29
<211> LENGTH: 16
<212> TYPE: PRT
<213> ORGANISM: Homo sapiens

<400> SEQUENCE: 29

Thr Ser Ser Ala Ser Thr Gly His Ala Thr Pro Leu Pro Val Thr Asp
1               5                   10                  15

<210> SEQ ID NO 30
<211> LENGTH: 8
<212> TYPE: PRT
<213> ORGANISM: Homo sapiens

<400> SEQUENCE: 30

Thr Thr Ser Thr Thr Ser Ala Pro
1               5

<210> SEQ ID NO 31
<211> LENGTH: 29
<212> TYPE: PRT
<213> ORGANISM: Homo sapiens

<400> SEQUENCE: 31

Ser Ser Thr Pro Gly Thr Ala His Thr Leu Thr Val Leu Thr Thr Thr
1               5                   10                  15

Ala Thr Thr Pro Thr Ala Thr Gly Ser Thr Ala Thr Pro
            20                  25

<210> SEQ ID NO 32
<211> LENGTH: 23
<212> TYPE: PRT
<213> ORGANISM: Homo sapiens

<400> SEQUENCE: 32

Thr Thr Ala Ala Pro Pro Thr Pro Ser Ala Thr Thr Pro Ala Pro Pro

```
1               5              10              15
Ser Ser Ser Ala Pro Pro Glu
            20

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 33

His His His His His His
1               5

<210> SEQ ID NO 34
<211> LENGTH: 13
<212> TYPE: PRT
<213> ORGANISM: Unknown
<220> FEATURE:
<223> OTHER INFORMATION: Description of Unknown:
      Muc6 mucin peptide
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (9)..(11)
<223> OTHER INFORMATION: Any amino acid

<400> SEQUENCE: 34

Thr Thr Ser Xaa Xaa Thr Xaa Ser Xaa Xaa Xaa Thr Thr
1               5                  10
```